(12) United States Patent
Naruse et al.

(10) Patent No.: US 11,384,172 B2
(45) Date of Patent: Jul. 12, 2022

(54) POLYMER, ANTIMICROBIAL AGENT, DISINFECTANT, ANTIMICROBIAL MATERIAL, DISINFECTANT MATERIAL, ANTIMICROBIAL METHOD, AND DISINFECTING METHOD

(71) Applicants: JSR CORPORATION, Minato-ku (JP); JAPAN AS REPRESENTED BY DIRECTOR-GENERAL OF NATIONAL INSTITUTE OF INFECTIOUS DISEASES, Shinjuku-ku (JP); JSR LIFE SCIENCES CORPORATION, Minato-ku (JP)

(72) Inventors: Hidenori Naruse, Minato-ku (JP); Atsushi Itou, Minato-ku (JP); Shigeru Ikawa, Minato-ku (JP); Tsutomu Shimokawa, Minato-ku (JP); Masato Suzuki, Shinjuku-ku (JP); Mari Matsui, Shinjuku-ku (JP); Satowa Suzuki, Shinjuku-ku (JP); Keigo Shibayama, Shinjuku-ku (JP); Kazuhiro Ikkyuu, Minato-ku (JP)

(73) Assignees: JSR CORPORATION, Minato-ku (JP); JAPAN AS REPRESENTED BY DIRECTOR-GENERAL OF NATIONAL INSTITUTE of INFECTIOUS DISEASES, Shinjuku-ku (JP); JSR LIFE SCIENCES CORPORATION, Minato-ku (JP)

( * ) Notice: Subject to any disclaimer, the term of this patent is extended or adjusted under 35 U.S.C. 154(b) by 337 days.

(21) Appl. No.: 16/061,809

(22) PCT Filed: Dec. 13, 2016

(86) PCT No.: PCT/JP2016/087108
§ 371 (c)(1),
(2) Date: Jun. 13, 2018

(87) PCT Pub. No.: WO2017/104676
PCT Pub. Date: Jun. 22, 2017

(65) Prior Publication Data
US 2018/0360033 A1 Dec. 20, 2018

(30) Foreign Application Priority Data
Dec. 14, 2015 (JP) .............................. JP2015-242866

(51) Int. Cl.
C08F 8/30 (2006.01)
C08F 20/70 (2006.01)
(Continued)

(52) U.S. Cl.
CPC ................ *C08F 8/30* (2013.01); *A01N 25/10* (2013.01); *A01N 25/34* (2013.01); *A01N 33/12* (2013.01);
(Continued)

(58) Field of Classification Search
CPC .......... C08F 20/34; C08F 20/36; C08F 20/70; C08F 22/22; C08F 26/06; C08F 26/08;
(Continued)

(56) References Cited

U.S. PATENT DOCUMENTS

| 5,100,969 A | * | 3/1992 | Yamamoto | ................ C08F 8/32 525/327.2 |
| 5,349,023 A | * | 9/1994 | Ikeda | ........................ C08F 8/32 525/330.5 |

(Continued)

FOREIGN PATENT DOCUMENTS

| CA | 2384427 A1 | 3/2001 |
| CN | 1671759 A | 9/2005 |
| CN | 101291580 A | 10/2008 |
| CN | 101743123 A | 6/2010 |

(Continued)

OTHER PUBLICATIONS

International Search Report dated Mar. 7, 2017 in PCT/JP2016/087108, filed on Dec. 13, 2016.
(Continued)

*Primary Examiner* — Ling Siu Choi
*Assistant Examiner* — David L Miller
(74) *Attorney, Agent, or Firm* — Oblon, McClelland, Maier & Neustadt, L.L.P.

(57) ABSTRACT

Provided is a polymer having antimicrobial and disinfecting properties against a wide range of kinds of germs. A polymer, including: a polymer chain having a repeating unit represented by the following formula (1); and a partial structure (excluding the polymer chain) derived from a compound containing a group represented by —NH—. [In formula (1), $R^1$ represents a hydrogen atom or a methyl group, Z represents a group forming an organic ammonium salt, —$NR^5R^6$ (where $R^5$ and $R^6$ each independently represent a hydrogen atom, or a substituted or unsubstituted hydrocarbon group), or a substituted or unsubstituted nitrogen-containing heterocyclic group, and X represents a single bond, or a divalent linking group.]

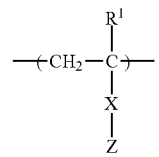

(1)

11 Claims, No Drawings

(51) Int. Cl.
| | |
|---|---|
| *C08F 20/34* | (2006.01) |
| *C08G 81/02* | (2006.01) |
| *C08F 220/34* | (2006.01) |
| *A01N 25/34* | (2006.01) |
| *A01N 25/10* | (2006.01) |
| *C08F 8/02* | (2006.01) |
| *C08F 8/44* | (2006.01) |
| *C08F 8/32* | (2006.01) |
| *C08F 222/22* | (2006.01) |
| *A01N 33/12* | (2006.01) |
| *C08L 5/00* | (2006.01) |
| *C08L 25/06* | (2006.01) |
| *C08L 67/04* | (2006.01) |
| *C08G 73/02* | (2006.01) |
| *C08F 4/48* | (2006.01) |
| *C08L 79/02* | (2006.01) |

(52) U.S. Cl.
CPC ............. *C08F 8/02* (2013.01); *C08F 8/32* (2013.01); *C08F 8/44* (2013.01); *C08F 20/34* (2013.01); *C08F 20/70* (2013.01); *C08F 220/34* (2013.01); *C08F 222/22* (2013.01); *C08G 81/024* (2013.01); *C08L 5/00* (2013.01); *C08L 25/06* (2013.01); *C08L 67/04* (2013.01); *C08F 4/48* (2013.01); *C08F 2800/20* (2013.01); *C08F 2810/40* (2013.01); *C08G 73/02* (2013.01); *C08L 79/02* (2013.01); *C08L 2203/02* (2013.01)

(58) Field of Classification Search
CPC ........ C08F 26/10; C08F 26/12; C08F 120/34; C08F 120/36; C08F 120/70; C08F 122/22; C08F 126/06; C08F 126/08; C08F 126/10; C08F 126/12; C08F 220/34; C08F 220/343; C08F 220/346; C08F 220/36; C08F 220/365; C08F 220/52; C08F 220/54; C08F 220/56; C08F 220/58; C08F 220/585; C08F 220/60; C08F 220/603; C08F 220/606; C08F 220/70; C08F 222/22; C08F 222/225; C08F 222/36; C08F 222/38; C08F 222/226; C08F 222/06; C08F 222/08; C08F 222/10; C08F 222/12; C08F 8/30; C08F 8/32

See application file for complete search history.

(56) References Cited

U.S. PATENT DOCUMENTS

| | | | |
|---|---|---|---|
| 5,631,336 A | * | 5/1997 | Ferruti ................. A61K 47/58 526/264 |
| 2002/0139583 A1 | | 10/2002 | Masui et al. |
| 2005/0003163 A1 | * | 1/2005 | Krishnan ............... A01N 37/44 428/190 |
| 2005/0265948 A1 | | 12/2005 | Ridley et al. |
| 2010/0048845 A1 | * | 2/2010 | Yasui ....................... C08F 8/00 526/204 |
| 2011/0136965 A1 | | 6/2011 | Murakami et al. |

FOREIGN PATENT DOCUMENTS

| | | | | |
|---|---|---|---|---|
| CN | 102046186 A | | 5/2011 | |
| JP | 53-6394 A | | 1/1978 | |
| JP | 02-36211 A | | 2/1990 | |
| JP | 09-154573 A | | 6/1997 | |
| JP | 2002-228558 A | | 8/2002 | |
| JP | 2003-34704 A | | 2/2003 | |
| JP | 2003-509546 A | | 3/2003 | |
| JP | 2006-96920 A | | 4/2006 | |
| JP | 2015-3958 A | | 1/2015 | |
| WO | WO 2010/16523 A1 | | 2/2010 | |
| WO | WO-2015017519 A1 | * | 2/2015 | ............. A61K 47/58 |

OTHER PUBLICATIONS

Combined Chinese Office Action and Search Report dated Dec. 27, 2019, in Patent Application No. 201680072789.9 (with English translation), 18 pages.

* cited by examiner

POLYMER, ANTIMICROBIAL AGENT, DISINFECTANT, ANTIMICROBIAL MATERIAL, DISINFECTANT MATERIAL, ANTIMICROBIAL METHOD, AND DISINFECTING METHOD

TECHNICAL FIELD

The present invention relates to a polymer, an antimicrobial agent, a disinfectant, an antimicrobial material, a disinfectant material, an antimicrobial method, and a disinfecting method.

BACKGROUND ART

An antimicrobial agent and a disinfectant are used in various fields of, for example, daily necessities, and medical products. For example, an antimicrobial agent and a disinfectant are used in a coating material for medical and hygiene products, a cleaning composition for clothing and contact lenses, and an antiseptic solution or an interior paint in food factories and hospitals. In addition, a material such as fibers, plastic, or film, to which an antimicrobial property and a disinfecting property are imparted by blending an antimicrobial agent and a disinfectant, is widely utilized.

As an antimicrobial and disinfecting polymer constituting such an antimicrobial agent, or a disinfectant, for example, a cationic polymer that has been proposed in Patent Literature 1 is known. Meanwhile, there is a problem that the antibacterial property and the disinfecting property are deteriorated when the concentration thereof is low.

CITATION LIST

Patent Literature

Patent Literature 1: JP 2003-509546 A

SUMMARY OF INVENTION

Technical Problem

Under the circumstances described above, the present applicant found that a copolymer having a weight average molecular weight of 3,000 or less containing, for example, a quaternary ammonium group has antimicrobial and disinfectant properties even at the low concentration, and previously filed a patent application (PCT/JP2015/069158). Meanwhile, antimicrobial and disinfectant properties against a wider range of kinds of germs are desired.

An object to be solved by the present invention is to provide a polymer having antimicrobial and disinfecting properties against a wide range of kinds of germs.

Solution to Problem

Accordingly, the inventors of the present invention conducted a thorough investigation, and as a result, the present inventors found that a polymer having a specific polymer chain and a specific partial structure has antimicrobial and disinfectant properties against a wide range of kinds of germs, and thus have completed the present invention.

That is, the present invention is to provide the following <1> to <12>.

<1> A polymer (hereinafter, also referred to as "specific polymer"), including: a polymer chain (hereinafter, also referred to as "specific polymer chain") having a repeating unit (hereinafter, also referred to as "repeating unit (1)") represented by the following formula (1); and a partial structure (excluding the polymer chain, and hereinafter, also referred to as "specific partial structure") derived from a compound containing a group (hereinafter, also referred to as "specific functional group") represented by —NH—.

[In formula (1),
$R^1$ represents a hydrogen atom or a methyl group,
Z represents a group forming an organic ammonium salt, —$NR^5R^6$ (where $R^5$ and $R^6$ each independently represent a hydrogen atom, or a substituted or unsubstituted hydrocarbon group), or a substituted or unsubstituted nitrogen-containing heterocyclic group, and
X represents a single bond, or a divalent linking group.]

<2> The polymer described in the above <1>, in which the partial structure is a residue obtained by removing a part or all of hydrogen atoms derived from the specific functional group from the compound.

<3> The polymer according to the above <1> or <2>, wherein a terminal of the polymer, chain is bonded to the partial structure.

<4> The polymer described in any one of the above <1> to <3>, in which the polymer chain further has a repeating unit represented by the following formula (2) (hereinafter, also referred to as "repeating unit (2)").

[In formula (2),
$R^7$ represents a hydrogen atom or a methyl group, and
A represents an aromatic hydrocarbon group, —(C=O)$OR^8$, —(C=O)$NHR^9$, or —$OR^{10}$ (where $R^8$ to $R^{10}$ each represent a hydrocarbon group or a group having a chain or cyclic ether structure).]

<5> The polymer according to any one of the above <1> to <4>, wherein the polymer chain is a polymer chain having an Mw (where Mw means weight average molecular weight in terms of polystyrene measured by gel permeation chromatography, and a mobile phase in the gel permeation chromatography is tetrahydrofuran) of 3,000 or less.

<6> The polymer described in any one of the above <1> to <5>, in which as the repeating unit represented by formula (1), the polymer chain has only a repeating unit (1) in which Z is —$N^+R^2R^3R^4Y^{y-}$ (where $R^2$ to $R^4$ each independently represent a hydrogen atom, or a substituted or unsubstituted hydrocarbon group, and $Y^{y-}$ represents a y-valent counter anion), or has a repeating unit (1) in which Z is —$N^+R^2R^3R^4Y^{y-}$ ($R^2$ to $R^4$ and $Y^{y-}$ have the same meanings as described above) and a repeating unit (1) in which Z is —$NR^5R^6$.

<7> The polymer according to any one of the above <1> to <6>, wherein X in the formula (1) is —(C=O)OR$^{11}$—(*), —(C=O)NHR$^{12}$—(*), or —ArR$^{13}$—(*) (where R$^{11}$ to R$^{13}$ each represent a methylene group, an alkylene group, or an alkylene oxyalkylene group, Ar represents an arylene group, and "*" represents a chemical bond bonded to the Z).

<8> The polymer according to any one of the above <1> to <7>, wherein the compound is a compound containing at least one kind selected from the group consisting of a primary amino group, a secondary amino group, and a carbamoyl group.

<9> The polymer according to any one of the above <1> to <8>, wherein the compound is a compound containing a plurality of groups represented by —NH—.

<10> The polymer according to any one of the above <1> to <9>, wherein the compound is a polyaziridine-based polymer, a modified polyaziridine-based polymer, a diamine-based compound, a biguanide-based compound, an amino acid, an amino acid derivative, a peptide, an amino sugar, a polyamino sugar, or an antimicrobial drug.

<11> The polymer according to any one of the above <1> to <10>, wherein the polymer chain has a divalent group formed by ring opening of a cyclic ether group, and the divalent group formed by ring opening of a cyclic ether group is bonded to the partial structure.

<12> An antimicrobial agent, a disinfectant, or an antimicrobial and disinfecting agent (hereinafter, also referred to as "antimicrobial and/or disinfecting agent"), including the polymer described in any one of the above <1> to <11> as an active component.

<13> An antimicrobial material, a disinfectant material, or an antimicrobial and disinfecting material (hereinafter, also referred to as "antimicrobial and/or disinfecting material"), including the polymer described in any one of the above <1> to <11>.

<14> An antimicrobial method, a disinfectant method, or an antimicrobial and disinfecting method (hereinafter, also referred to as "antimicrobial and/or disinfecting method"), including using the polymer described in any one of the above <1> to <11>.

Advantageous Effects of Invention

The polymer of the present invention has antimicrobial and disinfectant properties against a wide range of kinds of germs.

Description of Embodiments

[Specific Polymer]

At first, a specific polymer of the present invention will be described.

The specific polymer of the present invention has a polymer chain having a repeating unit represented by the following formula (1), and a partial structure (excluding the polymer chain) derived from a compound containing a group represented by —NH—.

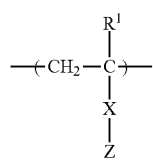

(1)

[In formula (1),

R$^1$ represents a hydrogen atom or a methyl group,

Z represents a group forming an organic ammonium salt, —NR$^5$R$^6$ (where R$^5$ and R$^6$ each independently represent a hydrogen atom, or a substituted or unsubstituted hydrocarbon group), or a substituted or unsubstituted nitrogen-containing heterocyclic group, and X represents a single bond, or a divalent linking group.]

(Repeating Unit (1))

A repeating unit (1) is represented by the above formula (1).

In the above formula (1), Z represents a group forming an organic ammonium salt, —NR$^5$R$^6$, or a substituted or unsubstituted nitrogen-containing heterocyclic group.

As the group forming an organic ammonium salt, for example, —N$^+$R$^2$R$^3$R$^4$Y$^{y-}$, —(C=O)O$^-$N$^+$HR$^2$R$^3$R$^4$, —(C=O)O$^-$A$^+$, or —OP(=O)(—O$^-$)OC$_2$H$_4$N$^+$R$^2$R$^3$R$^4$ (where R$^2$ to R$^4$ each independently represent a hydrogen atom, or a substituted or unsubstituted hydrocarbon group, Y$^{y-}$ represents a y-valent counter anion, and A$^+$ represents a quaternary ammonium cation) can be mentioned, and —N$^+$R$^2$R$^3$R$^4$Y$^{y-}$ is preferred.

R$^2$ to R$^6$ each independently represent a hydrogen atom, or a substituted or unsubstituted hydrocarbon group. Herein, the expression "hydrocarbon group" in the present invention is a concept including an aliphatic hydrocarbon group, an alicyclic hydrocarbon group, and an aromatic hydrocarbon group, and may be in any of linear, branched, and cyclic forms, may be a saturated hydrocarbon group or an unsaturated hydrocarbon group, or may have an unsaturated bond at either the terminal or the non-terminal.

As the above-described aliphatic hydrocarbon group, an alkyl group having 1 to 20 (preferably 1 to 12) carbon atoms is preferred. Specific examples of the aliphatic hydrocarbon group include a methyl group, an ethyl group, a n-propyl group, an isopropyl group, a n-butyl group, an isobutyl group, sec-butyl group, and a tert-butyl group. Further, as the above-described alicyclic hydrocarbon group, an alicyclic hydrocarbon group having 3 to 20 (preferably 3 to 12) carbon atoms is preferred, and a cycloalkyl group having 3 to 20 (preferably 3 to 12) carbon atoms is more preferred. Specific examples of the alicyclic hydrocarbon group include a cyclopropyl group, a cyclobutyl group, a cyclopentyl group, and a cyclohexyl group. Furthermore, as the above-described aromatic hydrocarbon group, an aromatic hydrocarbon group having 6 to 20 (preferably 6 to 10) carbon atoms is preferred, and an aryl group having 6 to 20 (preferably 6 to 10) carbon atoms, and an aralkyl group having 7 to 20 carbon atoms (preferably having 7 to 16 carbon atoms) are more preferred. Herein, the expression "aryl group" in the present invention is referred to as monocyclic to tricyclic aromatic hydrocarbon groups, and examples of the aryl group include a phenyl group, a naphthyl group, a biphenyl group, and an anthranyl group. Specific examples of the aralkyl group include a benzyl group, a phenethyl group, an α-methylbenzyl group, and a 2-phenylpropane-2-yl group.

Of these, as the hydrocarbon group in R$^2$ to R$^6$, from the viewpoint of the antibacterial property and the disinfecting property, an alkyl group having 1 to 12 (more preferably 1 to 6, and particularly preferably 1 to 4) carbon atoms, and an aralkyl group having 7 to 16 (more preferably 7 to 12, particularly preferably 7 to 9) carbon atoms are preferred, and a methyl group, an ethyl group, a n-propyl group, an isopropyl group, a n-butyl group, an isobutyl group, a sec-butyl group, a tert-butyl group, and a benzyl group, are particularly preferred.

In addition, examples of the substituent in $R^2$ to $R^6$ include an alkyl group having 1 to 6 carbon atoms, a halogen atom, a hydroxyl group, a benzoyl group, a substituted or unsubstituted amino group, a nitro group, a cyano group, a carboxyl group, and an alkoxy group having 1 to 6 carbon atoms.

$Y^{y-}$ may be a monovalent counter anion or a polyvalent counter anion. Further, $Y^{y-}$ may be a monoatomic anion or a polyatomic anion.

As the polyvalent counter anion, one derived from a polyvalent anionic compound can be mentioned. The expression "polyvalent anionic compound" is referred to as an organic or inorganic compound that is ionized to have a divalent or higher-valent negative charge when dissolved in water. Examples of the polyvalent anionic compound include a polymer compound such as gums, and a polyacrylic acid derivative, and a compound known as a chelating agent such as citric acid and a salt thereof, and EDTA.

Examples of the monovalent counter anion include a halogen ion such as $Cl^-$, $Br^-$, and $I^-$; and an acid counter anion such as $ClO_4^-$, $BF_4^-$, $CH_3(C=O)O^-$, and $PF_6^-$.

As the $Y^{y-}$, a monovalent to hexavalent counter anion (y is an integer of 1 to 6) is preferred, a monovalent to trivalent counter anion (y is an integer of 1 to 3) is more preferred, and a monovalent counter anion is furthermore preferred, and a halogen ion is particularly preferred.

In addition, the expression "nitrogen-containing heterocyclic group" in the present invention is referred to as a heterocyclic group having at least one nitrogen atom as a constituent of the ring, and a heteromonocyclic group, or a condensed heterocyclic group formed by condensation of two heteromonocyclic groups are preferred. The heterocyclic group may be an unsaturated ring or a saturated ring, and may have a hetero atom (for example, an oxygen atom, a sulfur atom) other than the nitrogen atom in the ring.

Examples of the unsaturated heterocyclic ring include a pyridine ring, an imidazole ring, a triazole ring, an oxazole ring, a triazole ring, a tetrazole ring, an imidazoline ring, and a tetrahydropyrimidine ring. Further, examples of the saturated heterocyclic ring include a morpholine ring, a piperidine ring, a piperazine ring, and a pyrrolidine ring. In addition, examples of the substituent in the nitrogen-containing heterocyclic group include an alkyl group having 1 to 6 carbon atoms, a halogen atom, a carboxyl group, an ester group, an ether group, a hydroxyl group, an amino group, an amide group, a thiol group, and a thioether group.

As the above-described heteromonocyclic group, a 5 to 7-membered ring is preferred, and specifically, a group having a basic skeleton represented by the following formula (1-1) or (1-2) can be mentioned. The heteromonocyclic group may have a substituent.

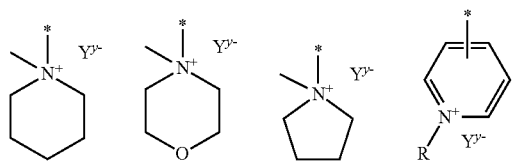

(1-1)

In formula (1-1) R represents a hydrogen atom, or a substituted or unsubstituted hydrocarbon group, $Y^{y-}$ represents a y-valent counter anion, and "*" represents a chemical bond. As the hydrocarbon group for R, one similar to that described above for $R^2$ can be mentioned, and as the $Y^{y-}$, one similar to $Y^{y-}$ in the above-described $-N^+R^2R^3R^4Y^{y-}$ can be mentioned.

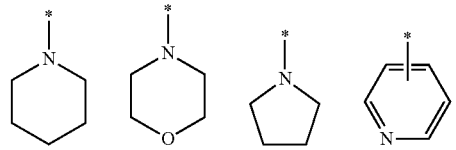

(1-2)

In formula (1-2), "*" represents a chemical bond.

In addition, as the above-described condensed heterocyclic group, specifically a group having a basic skeleton represented by the following formulas (1-3) to (1-5) can be mentioned, and the condensed heterocyclic group may have a substituent.

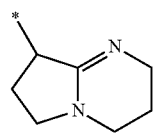

(1-3)

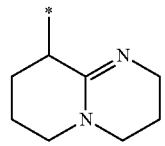

(1-4)

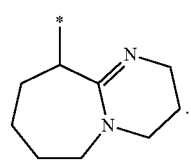

(1-5)

In formulas (1-3) to (1-5), "*" represents a chemical bond.

In the above-described formula (1), as the divalent linking group represented by X, for example, a methylene group, an alkylene group, an arylene group, $-(C=O)OR^{11}-(*)$, $-(C=O)NHR^{12}-(*)$, or $-ArR^{13}-(*)$ (where Ar represents an arylene group, and "*" represents a chemical bond bonded to the Z) can be mentioned. Examples of the "arylene group" in the present invention lude a phenylene group, a naphthylene group, and a phenanthrenylene group. In addition, $R^{11}$ to $R^{13}$ each represent a methylene group, an alkylene group, or an alkylene oxyalkylene group.

As the X and the alkylene group represented by $R^{11}$ to $R^{13}$, an alkylene group having 2 to 10 carbon atoms (preferably 2 to 6, and more preferably 2 to 4 carbon atoms) is preferred. The alkylene group may be a linear chain or a branched chain, and specific examples of the alkylene group include an ethylene group, a propylene group, a trimethylene group, a tetramethylene group, a pentamethylene group, and a hexamethylene group.

Further, as the alkylene group contained in an alkylene oxyalkylene group, one similar to the above-described alkylene group is preferred. As the alkylene oxyalkylene group, a $C_{2-4}$alkyleneoxy$C_{2-4}$alkylene group is preferred, and specifically, for example, an ethylene oxyethylene group can be mentioned.

From the viewpoint of, for example, the ease of production of the specific polymer, as the X, —(C=O)OR$^{11}$—(*), —(C=O)NHR$^{12}$—(*), or —ArR$^{13}$—(*) is preferred, and —(C=O)OR$^{11}$—(*) is particularly preferred. Further, as R$^{11}$ to R$^{13}$, an alkylene group having 2 to 6 carbon atoms (more preferably 2 to 4 carbon atoms) is particularly preferred.

(Repeating Unit (2))

From the viewpoint of enhancing the desired effect, as the specific polymer chain, one having a repeating unit represented by the following formula (2) in addition to a repeating unit (1) is preferred.

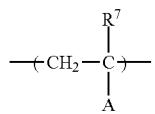
(2)

[In formula (2),

R$^7$ represents a hydrogen atom or a methyl group, and

A represents an aromatic hydrocarbon group, —(C=O)OR$^8$, —(C=O)NHR$^9$, or —OR$^{10}$ (where R$^8$ to R$^{10}$ each represent a hydrocarbon group or a group having a chain or cyclic ether structure).]

In A of the above-described formula (2), as the aromatic hydrocarbon group, an aryl group having 6 to 20 (preferably 6 to 10) carbon atoms is preferred, and a phenyl group is particularly preferred.

Further, in A of the above-described formula (2), R$^8$ to R$^{10}$ each represent a hydrocarbon group or a group having a chain or cyclic ether structure. As the hydrocarbon group, in addition to the one similar to the above-described R$^2$, an alicyclic hydrocarbon group such as a saturated condensed polycyclic hydrocarbon group, a saturated bridged cyclic hydrocarbon group, a saturated spiro hydrocarbon group, and a saturated cyclic terpene hydrocarbon group can be mentioned. As the hydrocarbon group of R$^8$ to R$^{10}$, an alkyl group having 1 to 20 (preferably 1 to 15) carbon atoms, an aryl group having 6 to 20 (preferably 6 to 14) carbon atoms, an aralkyl group having 7 to 20 carbon atoms (preferably 7 to 16 carbon atoms), and an alicyclic hydrocarbon group having 3 to 20 (preferably 4 to 15) carbon atoms are preferred, and a methyl group, an ethyl group, a n-propyl group, an isopropyl group, a n-butyl group, an isobutyl group, a sec-butyl group, a tert-butyl group, a 2-ethylhexyl group, an isodecyl group, a dodecyl group, a phenyl group, a benzyl group, a phenylethyl group, a cyclohexyl group, a cyclohexenyl group, a t-butyl cyclohexyl group, a decahydro-2-naphthyl group, a tricyclo[5.2.1.0$^{2,6}$]decane-8-yl group, an adamantyl group, a dicyclopentenyl group, a pentacyclopentadecanyl group, a tricyclopentenyl group, an isobornyl group are particularly preferred.

On the other hand, as the group having a chain ether structure in R$^8$ to R$^{10}$, a group represented by the following formula (3) is preferred.

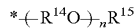
(3)

[In formula (3),

R$^{14}$ independently represents an alkylene group having 2 to 4 carbon atoms,

R$^{15}$ represents a hydrogen atom, an alkyl group having 1 to 6 carbon atoms, or a substituted or unsubstituted aryl group, n represents an integer of 2 to 150, and "*" represents a chemical bond.]

R$^{14}$ may be constituted of two or more kinds of alkylene groups, and is preferably an ethylene group and/or a propylene group.

As the alkyl group having 1 to 6 carbon atoms in R$^{15}$, an alkyl group having 1 to 4 carbon atoms is preferred, and an alkyl group having 1 or 2 carbon atoms is more preferred. The alkyl group may be a linear chain or a branched chain, and examples of the alkyl group include a methyl group, an ethyl group, a n-propyl group, an isopropyl group, a n-butyl group, an isobutyl group, a sec-butyl group, and a Cert-butyl group.

As the aryl group in R$^{15}$, a phenyl group is preferred. The aryl group may be substituted with, for example, an α-cumyl group.

As the R$^{15}$, a hydrogen atom, or an alkyl group having 1 to 6 carbon atoms is preferred.

As the n, an integer of 2 to 20 is preferred, an integer of 2 to 10 is more preferred, and an integer of 2 to 5 is particularly preferred.

In addition, as the group having a cyclic ether structure in R$^8$ to R$^{10}$, a group represented by the following formula (4) is preferred.

$$*—R^{16}—CE \quad (4)$$

[In formula (4),

R$^{16}$ represents a methylene group, or an alkylene group having 2 to 12 carbon atoms, CE represents a cyclic ether group that may have an alkyl group as a substituent, and "*" represents a chemical bond.]

In the above formula (4), as the R$^{16}$, a methylene group, and an alkylene group having 2 to 6 carbon atoms are preferred. The alkylene group may be a linear chain or a branched chain. Specific examples of the R$^{16}$ include a methylene group, an ethylene group, an ethane-1,1-diyl group, a trimethylene group, propane-1,1-diyl group, a propane-1,2-diyl group, a propane-2,2-diyl group, a tetramethylene group, a butane-1,2-diyl group, a butane-1,3-diyl group, a pentamethylene group, and a hexamethylene group.

In the above formula (4), as the CE, a cyclic ether group in which the number of atoms constituting the ring is 3 to 7 is preferred, and as a specific example, cyclic ether groups represented by the following formulas (i) to (viii) can be mentioned.

(i)

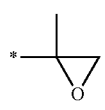
(ii)

(iii)

-continued

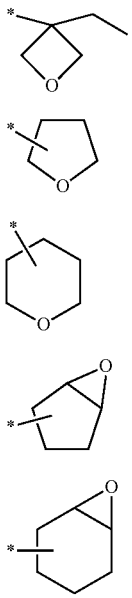

[In formulas (i) to (viii) "*" represents a chemical bond bonded to $R^{16}$.]

In the present invention, from the viewpoint of the effect of suppressing the growth of germs, as the above-described $R^8$ to $R^{10}$, a hydrocarbon group is preferred.

The specific polymer chain may have a repeating unit (hereinafter, referred to as "another repeating unit") other than the repeating units (1) and (2). As an example of the repeating unit as described above, a repeating unit derived from a vinyl-based monomer having an anionic group can be mentioned. Examples of the anionic group include a carboxyl group, a sulfonic acid group, a phosphoric acid group, and an anionic hydroxyl group. Of these, a carboxyl group, and a sulfonic acid group are preferred, and a carboxyl group is more preferred.

Suitable specific examples of the vinyl-based monomer having an anionic group include a vinyl-based monomer having an acidic group such as (meth)acrylic acid, maleic acid, maleic anhydride, styrenesulfonic acid, 2-(meth)acrylamide-2-methylpropanesulfonic acid, allylsulfonic acid, vinylsulfonic acid, (meth)acryl sulfonic acid, sulfopropyl (meth)acrylate, mono [2-(meth)acryloyloxyethyl] succinate, ω-carboxypolycaprolactone mono(meth)acrylate, p-vinylbenzoic acid, p-hydroxystyrene, and p-hydroxy-α-methyl styrene, and a salt thereof. These may be used singly alone, or in combination of two or more kinds thereof. Of these, (meth)acrylic acid, maleic acid, and maleic anhydride are preferred. In addition, as a monomer constituting another repeating unit, for example, an N-position substituted maleimide such as N-phenylmaleimide, and N-cyclohexylmaleimide; a (meth)acrylic acid ester having a hydroxyl group such as 2-hydroxyethyl (meth)acrylate, glycerol mono (meth)acrylate, and 4-hydroxyphenyl (meth)acrylate; and a (meth)acrylamide-based monomer such as (meth)acrylamide, and N-methylol acrylamide can be mentioned. The specific polymer chain may have one kind or two or more kinds thereof, which are corresponding to the other repeating unit.

Note that in the present invention, the expression "(meth) acrylate" means "acrylate or methacrylate".

In the specific polymer chain, the copolymerization proportion of the repeating unit (1) in all the repeating units is preferably 10 to 99% by mass, more preferably 15 to 95% by mass, and particularly preferably 20 to 90% by mass. The copolymerization proportion of the repeating unit (2) in all the repeating units is preferably 1 to 80% by mass, more preferably 5 to 75% by mass, and particularly preferably 10 to 70% by mass. By copolymerizing each of the repeating units at such a ratio, the desired effect can be further enhanced. In addition, as the mass ratio [(1)/(2)] of the copolymerization proportion of the repeating unit (1) to the copolymerization proportion of the repeating unit (2), 15/85 to 99/1 is preferred, 20/80 to 95/5 is more preferred, and 30/70 to 90/10 is particularly preferred.

In this regard, the copolymerization proportion and the copolymerization ratio can be measured by, for example, pyrolysis gas chromatography measurement. For example, in Synthesis Example 1 described later, peaks derived from DAMA, nBMA, MMA, and EHMA are identified and quantified from the peak fragments of respective chromatograms, and the copolymerization ratio can be calculated. An example of measurement conditions is shown below. Further, the copolymerization ratio can also be measured by NMR.

<Confirmation of Composition Ratio of Polymer>

Device: pyrolysis gas chromatogram mass spectrometer (thermal decomposition part: Pyrofoil Sampler JPS-350 manufactured by Japan Analytical Industry Co., Ltd., gas chromatograph part Agilent Technologies 7890A GC System, and mass spectrometer part: Agilent Technologies 5975 inert XL Mass Selective detector)

Column: BPX-5

Temperature: thermal decomposition temperature: 590° C.×5 seconds, column inlet: 280° C., column temperature (with the starting temperature set at 50° C., the temperature was raised to 350° C. by 10° C. per minute)

Flow rate: He 1.0 mL/min.

Ionization method: electron ionization method (EI method)

Detection part: MS quadrupole, Aux-2

The specific polymer chain may have one kind or two or more kinds of the ones, which are corresponding to the repeating unit (1), and may have one kind or two or more kinds of the ones, which are corresponding to the repeating unit (2), however, it is preferred that as the repeating unit (1), the specific polymer chain contains only the repeating unit (1) in which Z is a group forming an organic ammonium salt, or contains both of the repeating unit (1) in which Z is a group forming an organic ammonium salt, and the repeating unit (1) in which Z is —$NR^5R^6$.

Further, from the viewpoint of enhancing the desired effect, it is preferred that the repeating unit (1) contains the repeating unit in which Z is a group forming an organic ammonium salt in an amount of preferably 30% by mole or more, more preferably 40% by mole or more, furthermore preferably 50% by mole or more, and particularly preferably 60% by mole or more (note that the upper limit of the content is not particularly limited, and is, for example, 100% by mole). In a case where both of the repeating unit in which Z is a group forming an organic ammonium salt and the repeating unit in which Z is —$NR^5R^6$ are contained, the copolymerization ratio (mole ratio) of the repeating unit in which Z is a group forming an organic ammonium salt to the repeating unit in which Z is —$NR^5R^6$ is preferably 20/80 to 99/1, more preferably 30/70 to 98/2, and particularly preferably 40/60 to 95/5.

In a case where the specific polymer chain has the repeating unit (1) and the repeating unit (2), the specific polymer chain may be either a block copolymer, or a random copolymer, and is not particularly limited, however, from the viewpoint of enhancing the desired effect, a random copolymer is preferred.

In this regard, as the above-described block copolymer, a block copolymer containing a block A having no repeating unit (2) and having a repeating unit (1), and a block B having no repeating unit (1) and having a repeating unit (2) can be mentioned. As the block copolymer, an A-B type block copolymer can be mentioned. In the block A, as the repeating unit (1), two or more kinds of repeating units may be contained in one block A, and in that case, each of the repeating units may be contained in any form of random copolymerization and block copolymerization in the block A. Further, in a similar manner, in the block B, as the repeating unit (2), two or more kinds of repeating units may be contained in one block B, and in that case, each of the repeating units may be contained in any form of random copolymerization and block copolymerization in the block B.

With regard to the molecular weight of the specific polymer chain, the weight average molecular weight Mw in terms of polystyrene measured by gel permeation chromatography (GPC, mobile phase tetrahydrofuran) is preferably 3,000 or less, more preferably 300 to 3,000, and furthermore preferably 500 to 2,500. In addition, the ratio (Mw/Mn) of the Mw of the specific polymer chain to the number average molecular weight Mn in terms of polystyrene measured by GPC (mobile phase: tetrahydrofuran) is preferably 1.0 to 1.8, more preferably 1.0 to 1.7, and particularly preferably 1.1 to 1.5. By setting the specific polymer chain in such an embodiment, the desired effect can be enhanced.

In the specific polymer chain, it is preferred that the terminal is bonded to a specific partial structure, and in particular, it is preferred that the terminal is bonded to a N atom derived from a specific functional group in the specific partial structure. In addition, as the specific polymer chain, a polymer chain having a divalent group that is formed by ring opening of a cyclic ether group is preferred, and from the viewpoint of having a high reactivity, a polymer chain having a divalent group that is formed by ring opening of a cyclic ether group at the terminal of the polymer chain is more preferred. Further, as the specific polymer, a polymer in which the divalent group that is formed by ring opening of a cyclic ether group is bonded to a specific partial structure is preferred, and in particular, a polymer in which the divalent group that is formed by ring opening of a cyclic ether group is bonded to a N atom derived from a specific functional group in the specific partial structure is preferred.

As the divalent group that is formed by ring opening of a cyclic ether group, a divalent group that is formed by ring opening of a cyclic ether group in which the number of atoms constituting the ring is 3 to 7 is preferred, a divalent group that is formed by ring opening of a cyclic ether group represented by formulas (i-2) to (viii-2) is more preferred, and a divalent group (ring-opened epoxy group) that is formed by ring opening of a cyclic ether group represented by formula (i-2) is particularly preferred. In addition, a divalent group that is formed by ring opening of a cyclic ether group represented by formulas (i-2) to (iv-2) is specifically represented by the following formulas (i-3) to (iv-3).

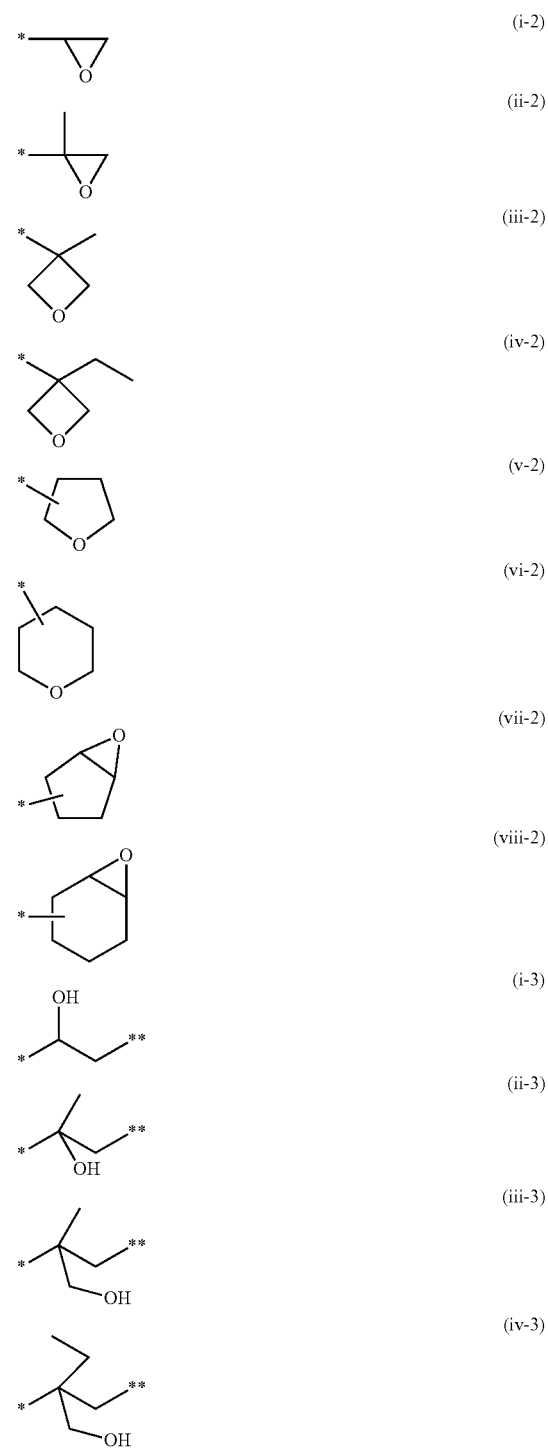

[In each formula, "*" represents a chemical bond bonded to the repeating unit (1) (the repeating unit (1) or (2) in a case where the specific polymer chain has the repeating unit (1) and the repeating unit (2)), and "**" represents a chemical bond bonded to the N atom derived from a specific functional group in the specific partial structure.]

In addition, the repeating unit (1) (the repeating unit (1) or (2) in a case where the specific polymer chain has the repeating unit (1) and the repeating unit (2)), and the divalent group that is formed by ring opening of a cyclic ether group may be bonded to each other via a divalent linking group.

As the divalent linking group, a methylene group, and an alkylene group having 2 to 12 carbon atoms are preferred. The alkylene group may be a linear chain or a branched chain. Specific examples of the divalent linking group include a methylene group, an ethylene group, an ethane-1,1-diyl group, a trimethylene group, a propane-1,1-diyl group, a propane-1,2-diyl group, a propane-2,2-diyl group, tetramethylene group, a butane-1,2-diyl group, a butane-1,3-diyl group, a pentamethylene group, and a hexamethylene group.

As the content of the specific polymer chain, relative to the total amount of the specific polymers, 40 to 99% by mass is preferred, 45 to 97% by mass is more preferred, and 50 to 95% by mass is particularly preferred.

In this regard, the content of the specific polymer chain can be measured by, for example, pyrolysis gas chromatography. For example, in Synthesis Example 1 described later, peaks corresponding to the specific polymer and the specific polymer chain are identified and quantified from the peak fragments of respective chromatograms, and the content of the specific polymer chain can be calculated. An example of measurement conditions is shown below. Further, the content of the specific polymer chain can also be measured by NMR.

<Confirmation of Composition Ratio of Polymer>

Device: pyrolysis gas chromatogram mass spectrometer (thermal decomposition part: Pyrofoil Sampler JPS-350 manufactured by Japan Analytical Industry Co., Ltd., gas chromatograph part: Agilent Technologies 7890A GC System, and mass spectrometer part: Agilent Technologies 5975 inert XL Mass Selective detector)

Column: SPX-5

Temperature: thermal decomposition temperature: 590° C.×5 seconds, column inlet: 280° C., column temperature (with the starting temperature set at 50° C., the temperature was raised to 350° C. by 10° C. per minute)

Flow rate: He 1.0 mL/min.

Ionization method: electron ionization method (EI method)

Detection part: MS quadrupole, Aux-2

(Specific Partial Structure)

The specific partial structure is a partial structure derived from a compound containing a specific functional group. However, the specific partial structure is a concept not including a specific polymer chain. it is preferred that the specific partial structure is a residue obtained by removing a part or all of hydrogen atoms derived from the specific functional group from the compound.

As the compound containing a specific functional group, from the viewpoint of the antibacterial property and the disinfecting property, a compound containing at least one kind selected from the group consisting of a primary amino group, a secondary amino group, a carbamoyl group (—C(=O)—NH$_2$), and an amide bond (—C(=O)—NH—) is preferred, a compound containing at least one kind selected from the group consisting of a primary amino group, a secondary amino group, and a carbamoyl group is more preferred, and a compound containing at least one kind selected from the group consisting of a primary amino group, and a secondary amino group is particularly preferred. In addition, the compound containing a specific functional group may also be a compound containing one specific functional group, or a compound containing multiple specific functional groups, and is preferably a compound containing multiple specific functional groups.

The specific partial structure may be a structure derived from a low molecular weight (non-polymer type) compound, or a structure derived from a high molecular weight (polymer type) compound. From the viewpoint of exhibiting excellent antimicrobial and disinfecting properties also against, for example, *Pseudomonas aeruginosa*, and of obtaining excellent antimicrobial and disinfecting properties against a wider range of kinds of germs, the specific partial structure is preferably a structure derived from a high molecular weight (polymer type) amine compound, and particularly preferably a structure derived from a multi-branched polymer among amine compounds. In a case where the amine compound is a multi-branched polymer, the specific polymer is a multi-branched star polymer that has a specific partial structure as the core part and has a specific polymer chain as the arm part. In addition, the weight average molecular weight of a polymer-type amine compound is preferably 100 or more, and more preferably 150 or more, and is preferably 3000 or less, more preferably 2500 or less, furthermore preferably 2000 or less, and particularly preferably 1500 or less.

Further, in a case where the compound containing a specific functional group is a compound containing at least one kind selected from the group consisting of a primary amino group and a secondary amino group, with regard to the specific partial structure, apart or all of the amino groups derived from a compound containing a specific functional group may be formed to be an organic ammonium salt.

In addition, examples of the compound containing the above-described specific functional group include a polyaziridine-based polymer; a modified polyaziridine-based polymer thereof such as a modified alkyl isocyanate, and a modified alkylene oxide; a diamine-based compound such as an aromatic diamine-based compound; a biguanide-based compound (may be a low molecular weight (non-polymer) or a high molecular weight (polymer)); an amino acid; an amino acid derivative; a peptide; amino sugar; polyamino sugar; and other antimicrobial drugs. Among the specific partial structures derived from these, the specific polymer may also have one kind or two or more kinds of the specific partial structures.

Of these, as the compound containing a specific functional group, a polyaziridine-based polymer, a diamine-based compound, a biguanide-based low-molecular compound, an amino acid, and an amino acid derivative are preferred, and from the viewpoint of exhibiting excellent antimicrobial and disinfecting properties also against, for example, *Pseudomonas aeruginosa*, and of obtaining excellent antimicrobial and disinfecting properties against a wider range of kinds of germs, a polyaziridine-based polymer, and a diamine-based compound are more preferred, a polyaziridine-based polymer, and an aromatic diamine-based compound are furthermore preferred, and a polyaziridine-based polymer is particularly preferred. In addition, similarly to the above, the weight average molecular weight of a polyaziridine-based polymer is preferably 100 or more, and more preferably 150 or more, and is preferably 3000 or less, more preferably 2500 or less, furthermore preferably 2000 or less, and particularly preferably 1500 or less. In addition, as described above, in a case where the compound containing a specific functional group is a polyaziridine-based polymer, the specific polymer is a multi-branched star polymer that has a specific partial structure as the core part and has a specific polymer chain as the arm part.

As the polyazyridine-based polymer, one having the repeating unit represented by the following formula (11) can be mentioned.

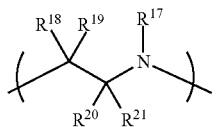

(11)

[In formula (11),
$R^{17}$ represents a chemical bond bonded to a hydrogen atom or another repeating unit (11), and
$R^{18}$ to $R^{21}$ each independently represent a hydrogen atom, or a substituted or unsubstituted hydrocarbon group.

With the proviso that in a case where $R^{18}$ and $R^{19}$ both are a hydrocarbon group, $R^{18}$ and $R^{19}$ together may form a ring, in a case where $R^{18}$ and $R^{20}$ both are a hydrocarbon group, $R^{18}$ and $R^{20}$ together may form a ring, and in a case where $R^{20}$ and $R^{21}$ both are a hydrocarbon group, $R^{20}$ and $R^{21}$ together may form a ring.]

In a case where $R^{17}$ is a chemical bond bonded to another repeating unit (11), formula (11) is specifically represented by the following formula (11-2). As the polyaziridine-based polymer, one having both of the repeating unit in which $R^{17}$ is a hydrogen atom and the trivalent repeating unit represented by formula (11-2) is preferred.

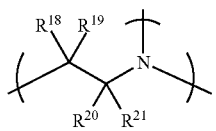

(11-2)

[In formula (11-2), $R^{18}$ to $R^{21}$ have the same meanings as those of $R^{18}$ to $R^{21}$ in formula (11).]

Similarly to the above $R^2$ to $R^6$, the hydrocarbon group represented by $R^{18}$ to $R^{21}$ is a concept including an aliphatic hydrocarbon group, an alicyclic hydrocarbon group, and an aromatic hydrocarbon group, and may be in any of linear, branched, and cyclic forms, may be a saturated hydrocarbon group or an unsaturated hydrocarbon group, or may have an unsaturated bond at either the terminal or the non-terminal. As the hydrocarbon group represented by $R^{18}$ to $R^{21}$, an aliphatic hydrocarbon group is preferred, and an alkyl group having 1 to 20 carbon atoms (preferably 1 to 12, and more preferably 1 to 4) is preferred. Specific examples of the hydrocarbon group represented by $R^{18}$ to $R^{21}$ include a methyl group, an ethyl group, a n-propyl group, an isopropyl group, a n-butyl group, an isobutyl group, a sec-butyl group, and a tert-butyl group.

In addition, as the ring that may be formed by each of the $R^{18}$ and $R^{19}$, the $R^{18}$ and $R^{20}$, and the $R^{20}$ and $R^{21}$, a cycloalkane ring having 3 to 10 carbon atoms such as a cyclohexane ring, a methylcyclohexane ring, a cycloheptane ring, and a cyclooctane ring can be mentioned.

As the substituent in $R^{18}$ to $R^{21}$, for example, an alkyl group having 1 to 6 carbon atoms, and a halogen atom can be mentioned.

Specific examples of the polyaziridine-based polymer include polyethyleneimine, polypropyleneimine, poly(2,2-dimethylaziridine), poly(2,3-dimethylaziridine), poly(2,2,3,3-tetramethylaziridine), poly(2-ethylaziridine), poly(2-hexylaziridine), poly(7-azabicyclo[4.1.0]heptane), poly(1-azaspiro[2.5]octane), poly(1-methyl-7-azabicyclo[4.1.0]heptane), and poly(3-methyl-7-azabicyclo[4.1.0]heptane). Of these, polyethyleneimine, and polypropyleneimine are preferred, and polyethyleneimine is particularly preferred.

As the diamine-based compound, a compound represented by the following (12) or (13) can be mentioned.

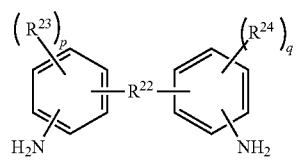

(12)

[In formula (12),
$R^{22}$ represents a single bond, an ether bond, an amide bond, an ester bond, a thio group, or a divalent organic group,
$R^{23}$ and $R^{24}$ each independently represent a substituted or unsubstituted hydrocarbon group, and
p and q each independently represent an integer of 0 to 4.

With the proviso that when $R^{22}$ is a divalent organic group, and further at least any one of p and q is an integer of 0 to 3, $R^{22}$ may form a condensed ring together with an adjacent phenylene group.]

$$H_2N—R^{25}—NH_2 \quad (13)$$

[In formula (13), $R^{25}$ represents a substituted or unsubstituted divalent aromatic hydrocarbon group, or a substituted or unsubstituted divalent nitrogen-containing heterocyclic group.]

In formula (12), $R^{22}$ represents a single bond, an ether bond, an amide bond, an ester bond, a thio group, or a divalent organic group. Of these, a single bond, an ether bond, a thio group, and a divalent organic group are preferred, and a divalent organic group is more preferred.

As the divalent organic group, a substituted or unsubstituted divalent hydrocarbon group, and a group in which a part of carbon atoms of the substituted or unsubstituted divalent hydrocarbon group is replaced with one or more kinds selected from the group consisting of an ether bond, an amide bond, an ester bond, and a thio group are more preferred, a substituted or unsubstituted divalent hydrocarbon group, and a group in which a part of carbon atoms of the substituted or unsubstituted divalent hydrocarbon group is replaced with one or more kinds selected from the group consisting of an ether bond, and an ester bond are furthermore preferred, and a group in which a part of carbon atoms of the substituted or unsubstituted divalent hydrocarbon group is replaced with an ester bond is particularly preferred. In addition, as the number of carbon atoms of the divalent organic group, 1 to 50 is preferred, 2 to 40 is more preferred, 3 to 30 is furthermore preferred, and 5 to 20 is particularly preferred. In this regard, in a group in which a part of carbon atoms of the substituted or unsubstituted divalent hydrocarbon group is replaced with one or more kinds selected from the group consisting of an ether bond, an amide bond, an ester bond, and a thio group, the number of an ether bond, an amide bond, an ester bond, and a thio group may be one, or two or more.

As the "divalent hydrocarbon group" in $R^{22}$, any one of a divalent aliphatic hydrocarbon group, a divalent alicyclic hydrocarbon group, and a divalent aromatic hydrocarbon group may be accepted. Further, a divalent group to which these hydrocarbon groups are linked may also be accepted.

As the number of carbon atoms of the above-described divalent aliphatic hydrocarbon group, 1 to 50 is preferred, 2 to 40 is more preferred, 3 to 30 is furthermore preferred, and 5 to 20 is particularly preferred. In this regard, the divalent aliphatic hydrocarbon group may be a linear chain or a branched chain. In addition, the divalent aliphatic hydrocarbon group may have an unsaturated bond in the molecule, and is preferably an alkanediyl group. Specific examples of the alkanediyl group include a methane-1,1-diyl group, an ethane-1,1-diyl group, an ethane-1,2-diyl group, a propane-1,1-diyl group, a propane-1,2-diyl group, a propane-1,3-diyl group, a propane-2,2-diyl group, a butane-1,1-diyl group, a butane-1,2-diyl group, a butane-1,3-diyl group, a butane-1,4-diyl group, a pentane-1,1-diyl group, a pentane-1,2-diyl group, a pentane-1,3-diyl group, pentane-1,4-diyl group, a pentane-1,5-diyl group, a hexane-1,1-diyl group, a hexane-1,2-diyl group, a hexane-1,3-diyl group, a hexane-1,4-diyl group, hexane-1,5-diyl group, a hexane-1,6-diyl group, heptane-1,7-diyl group, an octane-1,8-diyl group, a nonane-1,9-diyl group, and a decane-1,10-diyl group.

As the number of carbon atoms of the above-described divalent alicyclic hydrocarbon group, 3 to 20 is preferred, 3 to 16 is more preferred, 3 to 12 is furthermore preferred, and 3 to 8 is particularly preferred. Specifically, a cycloalkylene group such as a cyclopropylene group, a cyclobutylene group, a cyclopentylene group, and a cyclohexylene group can be mentioned.

As the number of carbon atoms of the above-described divalent aromatic hydrocarbon group, 6 to 18 is preferred, and 6 to 12 is more preferred. Specifically, for example, a phenylene group, a naphthylene group, a phenanthrene group, an anthrylene group, and further a fluorenylene group (divalent group derived from a fluorene ring) can be mentioned.

In this regard, the bonding position of the divalent alicyclic hydrocarbon group and the bonding position of the divalent aromatic hydrocarbon group may be on any carbon on the ring.

As the substituent in $R^{22}$, for example, an alkyl group having 1 to 6 carbon atoms, and a halogen atom can be mentioned.

In formula (12), $R^{23}$ and $R^{24}$ each independently represent a substituted or unsubstituted hydrocarbon group. Similarly to the above $R^2$ to $R^6$, the hydrocarbon group represented by $R^{23}$ and $R^{24}$ is a concept including an aliphatic hydrocarbon group, an alicyclic hydrocarbon group, and an aromatic hydrocarbon group, and may be in any of linear, branched, and cyclic forms, may be a saturated hydrocarbon group or an unsaturated hydrocarbon group, or may have an unsaturated bond at either the terminal or the non-terminal. As the hydrocarbon group represented by $R^{23}$ and $R^{24}$, an aliphatic hydrocarbon group is preferred, and an alkyl group having 1 to 20 carbon atoms (preferably 1 to 12, and more preferably 1 to 4) is preferred. Specifically, for example, a methyl group, an ethyl group, a n-propyl group, an isopropyl group, a n-butyl group, an isobutyl group, a sec-butyl group, and a tert-butyl group can be mentioned. As the substituent in $R^{23}$ and $R^{24}$, for example, a halogen atom can be mentioned.

In formula (12), p and q each independently represent an integer of 0 to 4. As the p and q, 0 or 1 is preferred, and 0 is more preferred. In this regard, in a case where p is an integer of 2 to 4, p pieces of $R^{23}$ may be the same as or different from each other, and in a case where q is an integer of 2 to 4, q pieces of $R^{24}$ may be the same as or different from each other.

In formula (13), $R^{25}$ represents a substituted or unsubstituted divalent aromatic hydrocarbon group, or a substituted or unsubstituted divalent nitrogen-containing heterocyclic group.

As the number of carbon atoms of the above-described divalent aromatic hydrocarbon group, 6 to 18 is preferred, and 6 to 12 is more preferred. Specifically, for example, a phenylene group, a naphthylene group, a phenanthrene group, an anthrylene group, and further a fluorenylene group (divalent group derived from a fluorene ring) can be mentioned.

As the number of carbon atoms of the above-described divalent nitrogen-containing heterocyclic group, 4 to 18 is preferred, and 4 to 10 is more preferred. Specifically, for example, a pyridinylene group (divalent group derived from a pyridine ring), a pyrimidinylene group (divalent group derived from a pyrimidine ring), an acridinylene group (divalent group derived from an acridine ring), and a divalent group derived from a carbazole ring can be mentioned.

In this regard, the bonding position of the divalent aromatic hydrocarbon group and the bonding position of the divalent nitrogen-containing heterocyclic group may be on any carbon on the ring.

As the substituent in $R^{25}$, for example, an alkyl group having 1 to 6 carbon atoms, a halogen atom, and a carboxyl group can be mentioned.

Specific examples of the diamine-based compound include bis(4-aminophenylethyl) adipate, 4,4'-diaminodiphenylmethane, 4,4'-diaminodiphenyl sulfide, 2,2'-dimethyl-4,4'-diaminobiphenyl, 2,2'-bis(trifluoromethyl)-4,4'-diaminobiphenyl, 4,4'-diaminodiphenyl ether, 2,2-bis[4-(4-aminophenoxy)phenyl]propane, 9,9-bis(4-aminophenyl)fluorene, 2,2-bis[4-(4-aminophenoxy)phenyl]hexafluoropropane, 2,2-bis(4-aminophenyl)hexafluoropropane, 4,4'-(p-phenylenediisopropylidene)bisaniline, 4,4'-(m-phenylenediisopropylidene)bisaniline, 1,4-bis(4-aminophenoxy)benzene, 4,4'-bis(4-aminophenoxy)biphenyl, 1-(4-aminophenyl)-2,3-dihydro-1,3,3-trimethyl-1H-indene-5-amine, 1-(4-aminophenyl)-2,3-dihydro-1,3,3-trimethyl-1H-indene-6-amine, p-phenylenediamine, 1,5-diaminonaphthalene, 2,7-diaminofluorene, 3,5-diaminobenzoic acid, 2,6-diaminopyridine, 3,4-diaminopyridine, 2,4-diaminopyrimidine, 3,6-diaminoacridine, and 3,6-diaminocarbazole.

The biguanide-based compound may have at least one biguanide skeleton in the molecule, and may be a low molecular compound containing one biguanide skeleton, or a compound that has multiple repeating units containing a biguanide skeleton, such as polyhexamethylene biguanide. Of these, from the viewpoint of enhancing the desired effect, a low molecular compound containing one biguanide skeleton is preferred. As the low molecular compound containing one biguanide skeleton, a compound represented by the following (14) can be mentioned.

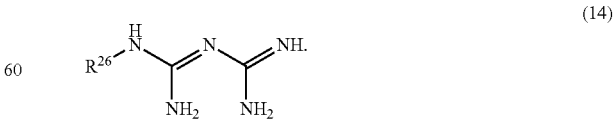

(14)

[In formula (14), $R^{26}$ represents an organic group.]

In formula (14), as the organic group represented by $R^{26}$, a substituted or unsubstituted hydrocarbon group is preferred.

Similarly to the above $R^2$ to $R^6$, the hydrocarbon group represented by $R^{26}$ is a concept including an aliphatic hydrocarbon group, an alicyclic hydrocarbon group, and an aromatic hydrocarbon group, and may be in any of linear, branched, and cyclic forms, may be a saturated hydrocarbon group or an unsaturated hydrocarbon group, or may have an unsaturated bond at either the terminal or the non-terminal.

As the above-described aliphatic hydrocarbon group, an alkyl group having 1 to 20 (preferably 1 to 12, more preferably 1 to 6, and particularly preferably 1 to 4) carbon atoms is preferred. Specifically, for example, a methyl group, an ethyl group, a n-propyl group, an isopropyl group, a n-butyl group, an isobutyl group, a sec-butyl group, and a tert-butyl group can be mentioned. Further, as the above-described alicyclic hydrocarbon group, an alicyclic hydrocarbon group having 3 to 20 (preferably 3 to 12) carbon atoms is preferred, and a cycloalkyl group having 3 to 20 (preferably 3 to 12) carbon atoms is more preferred. Specifically, for example, a cyclopropyl group, a cyclobutyl group, a cyclopentyl group, and a cyclohexyl group can be mentioned. Furthermore, as the above-described aromatic hydrocarbon group, an aromatic hydrocarbon group having 6 to 20 (preferably 6 to 10) carbon atoms is preferred, and an aryl group having 6 to 20 (preferably 6 to 10) carbon atoms, and an aralkyl group having 7 to 20 carbon atoms (preferably having 7 to 16 carbon atoms) are more preferred. The expression "aryl group" is referred to as a monocyclic to tricyclic aromatic hydrocarbon group, and example of the aryl group include a phenyl group, a naphthyl group, a biphenyl group, and an anthranyl group. Specific examples of the aralkyl group include a benzyl group, a phenethyl group, an α-methylbenzyl group, and a 2-phenylpropane-2-yl group.

Of these, as the hydrocarbon group in $R^{26}$, an alkyl group having 1 to 12 (more preferably 1 to 6, and particularly preferably 1 to 4) carbon atoms, and an aryl group having 6 to 10 carbon atoms are preferred, and an aryl group having 6 to 10 carbon atoms is particularly preferred.

In addition, examples of the substituent in $R^{26}$ include an alkyl group having 1 to 6 carbon atoms (such as a methyl group, an ethyl group, a n-propyl group, an isopropyl group, a n-butyl group, an isobutyl group, a sec-butyl group, and a tert-butyl group), a halogen atom, and an alkoxy group having 1 to 6 carbon atoms.

Suitable specific examples of the biguanide-based compound include ethyl biguanide, 1-butylbiguanide, 1-octadecylbiguanide, phenyl biguanide, 1-o-tolylbiguanide, 1-p-tolylbiguanide, 1-(2-phenylethyl)biguanide, 1-(2,3-xylyl) biguanide, and 1-(4-methoxylphenyl)biguanide.

In addition, as the amino acid, and the amino acid derivative, a known amino acid, and an amino acid derivative can be mentioned. Further, as the peptide and the antimicrobial drug, for example, a known oligopeptide, a polypeptide, and an antibiotic containing a peptide structure, a primary amino group, and a secondary amino group can be mentioned.

As the above-described amino acid derivative, N-acylamino acid is preferred, and N-alkanoylamino acid is more preferred. As the alkanoyl group in N-alkanoylamino acid, an alkanoyl group having 2 to 10 carbon atoms is preferred, and an alkanoyl group having 2 to 6 carbon atoms is more preferred. Specific examples of the alkanoyl group include an acetyl group, and a propionyl group. As the amino acid derivative, N-acetylamino acid is particularly preferred.

Specific examples of the amino acid, the amino acid derivative, the peptide, and the antimicrobial drug include lysine, glycine, alanine, glutamine, glutamic acid, N-acetyl-L-glutamine, N-acetyl-L-glutamic acid, polylysine, glycylglycine, glycylsarcosine, glutathione, L-alanyl-L-glutamine, daptomycin, vancomycin, colistin, ampicillin, cefditoren pivoxil, cephalosporin C, aztreonam, tigemonam, streptomycin, gentamicin, arbekacin, minocycline, tosufloxacin, trimethoprim, sulfamethoxazole, aciclovir, valacyclovir, lamivudine, and nystatin.

Further, examples of the amino sugar, and the polyamino sugar include glucosamine, galactosamine, mannosamine, hexosamine, and chitosan.

As the content of the specific partial structure, relative to the total amount of the specific polymers, 1 to 60% by mass is preferred, 3 to 55% by mass is more preferred, and 5 to 50% by mass is particularly preferred.

In addition, as the mass ratio of the content of the specific polymer chain to the content of the specific partial structure, 40/60 to 99/1 is preferred, 45/55 to 97/3 is more preferred, and 50/50 to 95/5 is particularly preferred.

In this regard, the content of the specific partial structure can be measured by, for example, pyrolysis gas chromatography.

Next, a method for producing a specific polymer will be described.

A specific polymer can be produced by appropriately combining known methods, and is preferably obtained by a method containing the following processes 1 and 2.

(Process 1): A process of bringing a polymer having the repeating unit (1) (preferably a copolymer having the repeating unit (1) and the repeating unit (2)) into contact with a compound having a cyclic ether group, and introducing the cyclic ether group into the polymer (Process 2): A process of bringing the cyclic ether group-containing compound obtained in Process 1 into contact with a compound containing a specific functional group, and allowing the cyclic ether group to react with the specific functional group (Process 1)

Process 1 is a process of bringing a polymer having the repeating unit (1) into contact with a compound having a cyclic ether group, and introducing the cyclic ether group into the polymer.

As the polymer having the repeating unit (1), a commercially available product, ora polymer obtained by chemical synthesis may be used, and the polymer having the repeating unit (1) is preferably produced by living polymerization of the monomer providing each of the above-described repeating units. As the living polymerization method, a known method such as living radical polymerization, or living anionic polymerization can be employed.

As the monomer that provides the repeating unit (1) and in which Z in formula (1) is a group forming an organic ammonium salt or —$NR^5R^6$, for example, (meth)acrylic acid esters containing an ammonium salt-type cationic functional group or an amino group, such as (meth)acryloyl aminopropyl trimethylammonium chloride, (meth)acryloyloxyethyl trimethylammonium chloride, (meth)acryloyloxyethyl triethylammonium chloride, (meth)acryloyloxyethyl (4-benzoylbenzyl)dimethylammonium bromide, (meth)acryloyloxyethyl benzyldimethylammonium chloride, (meth)acryloyloxyethyl benzyldiethylammonium chloride, dimethylaminoethyl (meth)acrylate, diethylaminoethyl (meth)acrylate, dimethylaminopropyl (meth)acrylate, and diethylaminopropyl (meth)acrylate; and (meth)acrylamides corresponding thereto can be mentioned.

In addition, the repeating unit (1) in which Z is a group forming an organic ammonium salt is preferably obtained by copolymerizing a monomer in which Z is —$NR^5R^6$ (for example, dimethylaminoethyl (meth)acrylate) or performing Process 1, or performing Process 2, and then by performing a reaction with a halogenated hydrocarbon compound such as benzyl chloride and quaternizing the amino group, and in particular, is preferably obtained by performing Process 2 and then quaternizing the amino group.

Further, as the monomer that provides the repeating unit (1) and in which Z in formula (1) is a nitrogen-containing heterocyclic group, for example, a compound group α (monomers 1 to 18) of the following formulas, a compound represented by the following formula (5), 4-vinylpyridine, and a salt thereof can be mentioned. In addition, the monomers providing the repeating unit (1) can be used alone or in combination of two or more kinds thereof.

[Compound Group α]

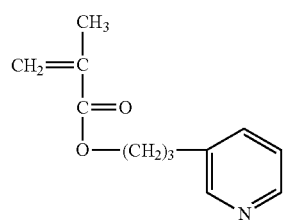
(Monomer 1)

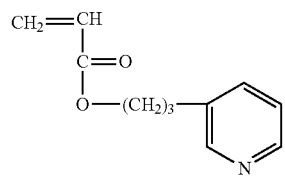
(Monomer 2)

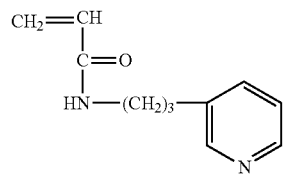
(Monomer 3)

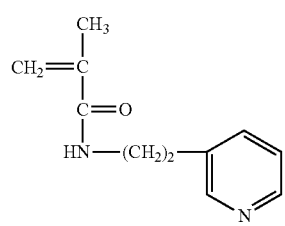
(Monomer 4)

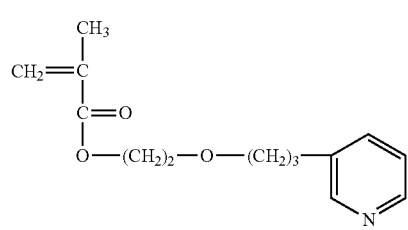
(Monomer 5)

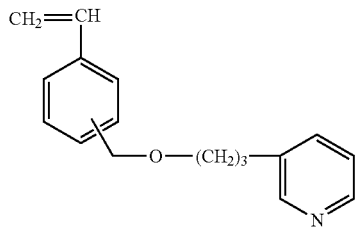
(Monomer 6)

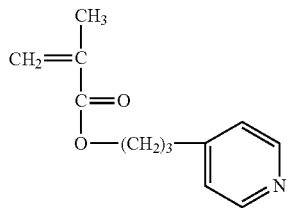
(Monomer 7)

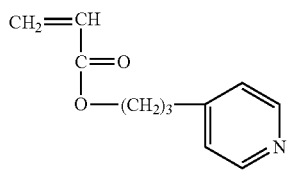
(Monomer 8)

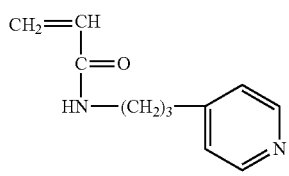
(Monomer 9)

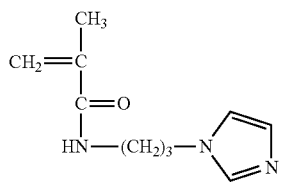
(Monomer 10)

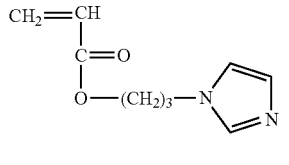
(Monomer 11)

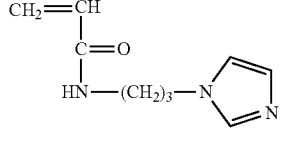
(Monomer 12)

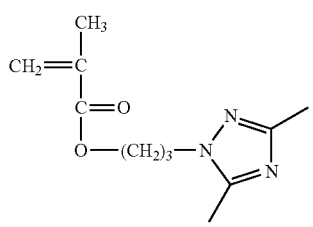
(Monomer 13)

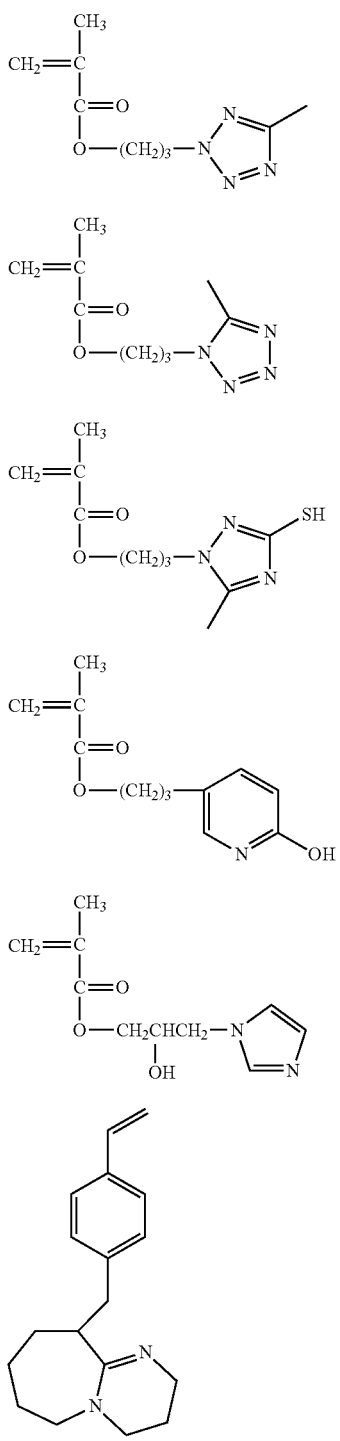

(Monomer 14)
(Monomer 15)
(Monomer 16)
(Monomer 17)
(Monomer 18)
(5)

In addition, as the monomer that provides the repeating unit (2), for example, styrene, and α-methylstyrene can be mentioned as a monomer providing the repeating unit (2) in which A is an aromatic hydrocarbon group. Further, examples of the monomer providing the repeating unit (2) in which $R^8$ to $R^{10}$ is a hydrocarbon group include (meth) acrylic acid esters such as methyl (meth)acrylate, ethyl (meth)acrylate, propyl (meth)acrylate, isopropyl(meth)acrylate, butyl(meth)acrylate, isobutyl (meth)acrylate, t-butyl (meth)acrylate, 2-ethylhexyl (meth)acrylate, isodecyl (meth)acrylate, dodecyl (meth)acrylate, cyclohexyl (meth) acrylate, t-butylcyclohexyl (meth)acrylate, cyclohexenyl (meth)acrylate, tricyclo[5.2.1.0$^{2,6}$]decane-8-yl (meth)acrylate, dicyclopentenyl (meth)acrylate, isobornyl (meth)acrylate, adamantyl (meth)acrylate, decahydro-2-naphthyl (meth)acrylate, and pentacyclopentadecanyl (meth)acrylate; (meth)acrylamides corresponding thereto; and vinyl ethers such as ethyl vinyl ether. Furthermore, examples of the monomer providing the repeating unit (2) in which $R^8$ to $R^{10}$ is a group having a chain or cyclic ether structure include (meth)acrylic acid esters having a chain or cyclic ether structure, such as polyethylene glycol (n=2 to 10) methyl ether (meth)acrylate, polypropylene glycol (n=2 to 10) methyl ether (meth)acrylate, polyethylene glycol (n=2 to 10) ethyl ether (meth)acrylate, polypropylene glycol (n=2 to 10) ethyl ether (meth)acrylate, polyethylene glycol (n=2 to 10) mono(meth)acrylate, polypropylene glycol (n=2 to 10) mono (meth)acrylate, ethylene oxide-modified (meth)acrylate of p-cumylphenol, glycidyl (meth)acrylate, 3,4-epoxycyclohexylmethyl (meth)acrylate, 3-[(meth)acryloyloxymethyl]oxetane, 3-[(meth)acryloyloxymethyl]-3-ethyloxetane, and tetrahydrofurfuryl (meth)acrylate; (meth) acrylamides corresponding thereto; and vinyl ethers such as 3-(vinyloxymethyl)-3-ethyloxetane. These can be used alone or in combination of two or more kinds thereof.

In addition, examples of the monomer providing a repeating unit other than the repeating unit (1) and the repeating unit (2) include a vinyl-based monomer having an acidic group such as (meth)acrylic acid, maleic acid, maleic anhydride, styrenesulfonic acid, 2-(meth)acrylamide-2-methylpropanesulfonic acid, allylsulfonic acid, vinylsulfonic acid, (meth)acryl sulfonic acid, sulfopropyl (meth)acrylate, mono [2-(meth)acryloyloxyethyl] succinate, ω-carboxypolycaprolactone mono(meth)acrylate, p-vinylbenzoic acid, p-hydroxystyrene, and p-hydroxy-α-methyl styrene; an N-position substituted maleimide such as N-phenylmaleimide, and N-cyclohexylmaleimide; a (meth)acrylic acid ester having a hydroxyl group such as 2-hydroxyethyl (meth)acrylate, glycerol mono(meth)acrylate, and 4-hydroxy phenyl (meth) acrylate; and a (meth)acrylamide-based monomer such as (meth)acrylamide, and N-methylol acrylamide. These can be used alone or in combination of two or more kinds thereof.

The compound having a cyclic ether group may be any one capable of introducing a cyclic ether group into a polymer having the repeating unit (1), and examples of the compound having a cyclic ether group include an epihalohydrin such as epichlorohydrin, epibromohydrin, epifluorohydrin, and epiiodohydrin. These can be used alone or in combination of two or more kinds thereof.

The amount to be used of the compound having a cyclic ether group is usually around 0.05 to 0.2 molar equivalents relative to the amount of the polymer having the repeating unit (1).

The reaction time of Process 1 is usually 0.5 to 2.5 hours, and the reaction temperature is usually −78 to 20° C.

(Process 2)

Process 2 is a process of bringing the cyclic ether group-containing compound obtained in Process 1 into contact with a compound containing a specific functional group, and allowing the cyclic ether group to react with the specific functional group.

As the compound containing a specific functional group, one mentioned as the one providing a specific partial structure may be used.

The amount to be used of the compound containing a specific functional group is usually around 0.7 to 1.3 molar equivalents relative to the amount of the cyclic ether group-containing polymer.

Process 2 may be performed in the presence of an organic phosphorus compound. As the organic phosphorus compound, triphenylphosphine such as triphenylphosphine, tris(3-methylphenyl)phosphine, tris(4-methylphenyl)phosphine, tris(3,5-dimethylphenyl)phosphine, diphenyl(pentafluorophenyl)phosphine, tris(pentafluorophenyl)phosphine, tris(4-chlorophenyl)phosphine, and tris[4-(methylthio)phenyl]phosphine, or a derivative thereof is preferred. These can be used singly alone or in combination of two or more kinds thereof.

The reaction time of Process 2 is usually 10 to 40 hours, and the reaction temperature is usually 40 to 80° C.

In addition, each of the above processes may be performed in the presence or absence of a solvent. Examples of the solvent include water; alcohols such as methanol, ethanol, propanol, isopropyl alcohol, n-butyl alcohol, isobutyl alcohol, sec-butyl alcohol, and t-butyl alcohol; an ethylene glycol derivative such as ethylene glycol, ethylene glycol monomethyl ether, ethylene glycol monoethyl ether, ethylene glycol monopropyl ether, ethylene glycol monobutyl ether, ethylene glycol monoethyl ether acetate, diethylene glycol monomethyl ether, diethylene glycol monoethyl ether, diethylene glycol dimethyl ether, and diethylene glycol diethyl ether; a propylene glycol derivative such as propylene glycol, propylene glycol monomethyl ether, propylene glycol monoethyl ether, propylene glycol monopropyl ether, propylene glycol monobutyl ether, and propylene glycol monomethyl ether acetate; ketones such as acetone, methyl ethyl ketone, methyl isobutyl ketone, methyl amyl ketone, diisobutyl ketone, and cyclohexanone; esters such as ethyl acetate, butyl acetate, isobutyl acetate, ethyl lactate, and γ-butyl lactone; amides such as N,N-dimethylformamide, N,N-dimethylacetamide, N-methylpyrrolidone, hexamethylphosphoric triamide, 1,3-dimethyl-2-idazoline, N,N'-dimethylpropyleneurea, tetramethylurea, and N-methylpyrrolidone; sulfoxides such as dimethyl sulfoxide; an aromatic hydrocarbon such as toluene, xylene, and nitrobenzene; ethers such as tetrahydrofuran, 1,3-dioxolane, diethyl ether, and morpholine, and these may be used singly alone, or in combination of two or more kinds thereof.

Further, in each of the above processes, isolation of each of the reaction products may be performed by appropriately combining ordinary means such as filtration, washing, drying, recrystallization, reprecipitation, dialysis, centrifugation, extraction with various kinds of solvents, neutralization, and chromatography, as needed.

In addition, the specific polymer has antimicrobial and disinfecting properties against a wide range of kinds of germs, and further has low cytotoxicity. Further, the specific polymer also has sufficient water solubility and dispersibility.

Accordingly, the specific polymer can be used, for example, as it is or in combination of other components, as an antimicrobial agent and/or a disinfectant, or an antimicrobial material and/or a disinfectant material.

[Antimicrobial Agent and/or Disinfectant]

The antimicrobial agent and/or disinfectant of the present invention contains a specific polymer as an active component. From the viewpoint of enhancing the desired effect and suppressing the cytotoxicity, the content of the specific polymer is, relative to the total amount of the antimicrobial agent and/or the disinfectant, preferably $10^{-8}$ to 10% by mass, more preferably 0.0001 to 5% by mass, furthermore preferably 0.005 to 1% by mass, and particularly preferably 0.001 to 0.1% by mass.

The antimicrobial agent and/or disinfectant of the present invention has antimicrobial and disinfectant properties against a wide range of kinds of germs. The antimicrobial agent and/or disinfectant of the present invention is particularly useful for suppressing the growth of bacteria.

Examples of the bacteria include Gram-positive bacteria, and Gram-negative bacteria, and the antimicrobial agent and/or disinfectant of the present invention can perform antimicrobial action and disinfecting action against both of the Gram-positive bacteria and the Gram-negative bacteria.

Examples of the Gram-positive bacteria include *Staphylococcus* such as *Staphylococcus aureus*; *Listeria* bacteria; *Bacillus* bacteria; and *Alicyclobacillus* bacteria. Further, examples of the Gram-negative bacteria include *Escherichia* bacteria such as *Escherichia coli* (*E. coli*); *Salmonella* bacteria; *Vibrio* bacteria; *Pseudomonas* bacteria such as *Pseudomonas aeruginosa*; *Acinetobacter* bacteria such as *A. baumannii*; and *Klebsiella* bacteria such as *Klebsiella pneumoniae*. Moreover, the antimicrobial agent and/or disinfectant of the present invention is also effective against resistant bacteria such as methicillin-resistant *Staphylococcus aureus* (MRSA).

[Antimicrobial Material and/or Disinfecting Material]

The antimicrobial material and/or disinfecting material of the present invention contains a specific polymer, and is a material in any form of, for example, solution, dispersion, gel, capsules, pellets, film, sheet, or fibers, in which the specific polymer is used in combination with other components.

For example, by using the specific polymer in combination with, for example, a solvent such as water, and an organic solvent; a surfactant such as an anionic surfactant, a cationic surfactant, and a nonionic surfactant; a thickener such as gelatin, polysaccharides, and cellulose; or a curable monomer such as a polyfunctional acrylate, and a polyfunctional epoxy compound, a coating material for antimicrobial action and/or disinfecting action can be obtained. From the viewpoint of the mixing stability and the functional expression, the specific polymer is preferably mixed in an aqueous coating material that has been disclosed in, for example, JP 2004-10779 A, JP 2008-248014 A, JP 9-111151 A, or JP 2012-149141 A to be used.

The coating material for antimicrobial action and/or disinfecting action can be used as, for example, a coating material for a medical article such as a medical device, and a medical appliance; a coating material for daily necessities such as toilet articles, and kitchen utensils; a coating material for a household electric appliance such as a personal computer, an air conditioner, and a refrigerator; and a coating material for a ship hull or a touch screen panel in addition to an interior paint, for example, on an inner wall of a house and a floor material of a house, and in a hospital, a facility for the elderly, and a food factory.

In addition, by mixing the specific polymer with an organic polymer material such as polyolefin, polyurethane, ABS, polystyrene, polycarbonate, polyester, polyamide, acrylic polymer, vinyl chloride, silicone, and cellulose, or by subjecting a formed body produced from these organic polymer materials or an inorganic material such as metal, and ceramics to a surface treatment with the specific polymer, the specific polymer can be used as a material, for example, for plastic, film, fibers, rubber, ceramics, or glass, to which an antimicrobial property and/or a disinfecting property is imparted. Such a material can be used for, for example, a medical supply such as a mask, a surgical gown, surgical cover cloth, a blood bag, and a wound dressing material; a daily necessity such as a bed sheet, a towel, a garbage can, a triangular corner, and a chair; or a touch panel device such as a smartphone, a tablet terminal, and a car navigation system. Further, such a material can be used as a building material such as wallpaper, a tile, and a doorknob; or a packaging material for a food and drink, or a medical appliance (for example, a PET bottle).

[Antimicrobial Method and/or Disinfecting Method]

The antimicrobial method and/or disinfecting method of the present invention uses a specific polymer.

The method is not particularly limited, and for example, a method including a process of applying a liquid composition containing the specific polymer and a solvent onto a surface of an object can be mentioned, and according to the method, an antimicrobial property and/or a disinfecting property can be imparted to the object. At this time, into the liquid composition containing the specific polymer, a solvent, and further, for example, a surfactant, a thickener, and a curable monomer can be mixed. As the means for the application, an ordinary means for application such as spray coating, coater coating, dipping, brushing, and roll coating can be employed. Further, examples of the object include a base material such as film, a resin substrate, fibers, ceramics, metal, glass, and wood; an interior part such as wall, floor, and ceiling; a medical appliance such as a catheter, an infusion tube, a blood bag, and a dressing; and eating or kitchen utensils such as tableware. From the viewpoint of enhancing the desired effect and suppressing the cytotoxicity, the content of the specific polymer is, relative to the total amount of the liquid composition, preferably $10^{-8}$ to 10% by mass, more preferably 0.0001 to 5% by mass, furthermore preferably 0.005 to 1% by mass, and particularly preferably 0.001 to 0.1% by mass.

In addition, by a method including a process of spraying a liquid composition containing the above-described specific polymer onto an object using, for example, a spray, an antimicrobial property and/or a disinfecting property can be imparted to the object, or the object can be disinfected. At this time, into the liquid composition containing the specific polymer, a solvent, and further, for example, a surfactant, and a fragrance can be mixed.

In addition, by a method including a process of washing an object with the use of a washing agent containing the above-described specific polymer, in addition to the washing of the object, the object can also be subjected to the antimicrobial action and/or the disinfecting action. At this time, the form of the washing agent is not particularly limited, and may be solid or liquid. Further, into the washing agent, similarly to the above, a solvent, and further, for example, a surfactant, and a fragrance can be mixed.

In addition, by a method including a process of immersing an object such as contact lenses in a liquid composition containing the above-described specific polymer, the object can be disinfected and sterilized. By a method including a process of impregnating a nonwoven fabric with a liquid composition containing the above-described specific polymer and wiping an object up with the nonwoven fabric, the object can also be disinfected and sterilized. At this time, into the liquid composition containing the specific polymer, a solvent, and further, for example, a surfactant, a fragrance, an enzyme, and a buffer solution can be mixed.

In addition, by a method including a process of mixing the specific polymer with an organic polymer material, the specific polymer can be used for a material, for example, for plastic, film, fibers, or rubber, to which an antimicrobial property and/or a disinfecting property is imparted.

Further, by adding the specific polymer of the present invention to a composition for producing a three-dimensional formed object such as an implant, a formed object to which an antimicrobial property or a disinfecting property is imparted can be produced. In addition, by using a coating material to which the specific polymer of the present invention has been added, coating may be performed onto a surface of a formed object produced as described above. Hereinafter, a production method of a formed object will be described using an implant for medical use as an example, however, the use method of the specific polymer of the present invention is not limited to the example, and can also be applied to a formed object that is used as any device.

With regard to an implant for medical use, for example, the shape of an application part (for example, affected part) in a dental treatment is grasped as stereoscopic information, by a method such as a tomographic imaging method using radiation such as CT scanning, or a nuclear magnetic resonance imaging method (MRI), and a formed object having a shape suitable for the treatment is produced by a lamination forming method on the basis of the information. At that time, by adding the specific polymer of the present invention into a composition to be a material for the formed object, an antimicrobial property and/or a disinfecting property can be imparted to the formed object. For example, the formed object can be produced by a forming method such as (a) a powder forming method by a laser (selective laser sintering method), (b) a powder fixation lamination method, (c) a fused deposition modeling method, (d) a thin-plate lamination method, or (e) a stereolithography method, and an embodiment in which the specific polymer of the present invention is added into a composition to be used in these forming methods is mentioned.

(a) As a powder forming method by a laser, for example, a three-dimensional powder forming method (selective laser sintering method using a laser) can be used. That is, according to the present method, powder having an average particle diameter of 0.001 to 0.3 mm, which contains the specific polymer of the present invention, is placed onto a support so as to be controlled on the basis of the dimensional information of a three-dimensional forming model that has been designed, for example, by CAD in advance, and to accurately correspond to the predetermined distance and thickness. The surface of the powder may be smoothed, for example, with a wiper as needed. Next, the powder is irradiated with a laser such as a carbon dioxide laser so as to form a shape corresponding to the model, and the powder is fused and solidified. By repeating this operation with the support being shifted in the vertical direction, an object corresponding to the model can be formed. As the laser used in the present forming method, it is not particularly limited, and for example, an infrared laser, a carbon dioxide laser, a solid-state laser such as an yttrium aluminum garnet (YAG) laser, or an excimer laser can be used. The output power and aperture of such a laser are appropriately selected depending on, for example, the biocompatible material to be used, and the shape of an object.

(b) In a powder fixation lamination method, for example, a method in which an inkjet technique as used, for example, in a printer is applied, and droplets as in a state of being heated and melted wax are continuously added dropwise, and deposited and solidified (deposition method); a method in which a binder is ejected from an inkjet head onto metal powder, ceramic powder, starch powder, or gypsum powder, and the powder is bonded to form the lamination (binder method); and a method in which resin powder is ejected from an inkjet head, and then cured by light (photocuring method) are included. The specific polymer of the present invention can be added, for example, to the droplets and the powder, which are described above. For example, multiple sectional views of an affected part, which are imaged in round slices, for example, by a tomographic imaging method using radiation such as CT scanning, or a nuclear magnetic resonance imaging method (MRI), are prepared, and a solidifying agent (for example, collagen, chondroitin sulfate, hyaluronic acid, and elastin) is sprayed onto a sheet on which powder has been spread thinly (for example, around 0.1 μm) in accordance with the sectional view by an inkjet technique as used, for example, in a printer so as to fix the powder to the sheet. This is a method in which the procedure described above is performed for each of the sectional views, and the obtained sheets are superimposed to produce a formed object having a desired shape.

(c) In a fused deposition modeling method, for example, there is a method in which the shape of a formed object to be produced is determined on the basis of the information of an affected part, which has been obtained, for example, by a tomographic imaging method using radiation such as CT scanning, or a nuclear magnetic resonance imaging method (MRI), a thermoplastic resin (for example, polycarbonate resin) to which the specific polymer of the present invention has been added is heated, while being continuously ejected (for example, linearly ejected) in a molten state from a nozzle, the heated thermoplastic resin is melted while scanning using, for example, an XY plotter system, and a molten material is extruded and solidified to laminate on a surface. In this method, the resins adhere to each other before curing.

(d) In a thin-plate lamination method, for example, there is a method in which the shape of a formed object to be produced is determined on the basis of the information of an affected part in a similar manner as in the case of the fused deposition modeling method (c), for example, a material in a sheet shape, which has been coated with an adhesive agent, is superimposed and compression bonded (for example, thermocompression bonded), for example, with rollers, an unnecessary part of a contour of the resultant material is cut off by means of, for example, a laser, or a knife, and this procedure is repeated to produce a membrane having a desired shape. In the present method, an embodiment in which the specific polymer of the present invention is added to an adhesive agent or a sheet can be mentioned.

(e) In a stereolithography method, for example, there is a method in which a photocurable resin in a liquid state is cured and laminated one by one with a light beam such as a laser, and a formed object in a three-dimensional shape is produced. In this forming method, a complicated shape can also be easily prepared, and a formed object with a high dimensional accuracy can be produced. In the present method, an embodiment in which the specific polymer of the present invention is added to a photocurable resin in a liquid state can be mentioned.

EXAMPLES

Hereinafter, the present invention will be described in detail with reference to Examples, however, the present invention is not limited to these Examples.

Abbreviations of, for example, the raw materials used in Examples are as follows.
THF: tetrahydrofuran
PGMEA: propylene glycol monomethyl ether acetate
MMA: methyl methacrylate
nBMA: n-butyl methacrylate (normal butyl methacrylate)
DAMA: dimethylaminoethyl methacrylate
EHMA: 2-ethylhexyl methacrylate <Measurement Conditions of Mw and Mw/Mn>

Mw and Mn, which measured in the following respective Synthesis Examples, are measured values in terms of polystyrene by gel permeation chromatography with the following specifications.
Device: GPC-104 (manufactured by SHOWA DENKO K.K.)
Column: Three columns of LF-604 were connected with KF-602 to be used
Mobile phase: THF
Temperature: 40° C.
Flow rate: 0.6 mL/min.

<Synthesis of Polymer>

Synthesis Example 1

Into a 300 mL flask, 125 mL of THF, 1.31 g of lithium chloride, and 3.8 g of diisopropylamine were added, the resultant mixture was cooled down to −60° C., and then into the cooled mixture, 23.5 mL of a hexane solution of n-butyl-lithium (at a concentration of 1.6 mol/L) was added, and the mixture was stirred for 15 minutes. Subsequently, into the resultant mixture, 3.8 g of methyl isobutyrate was added, and the mixture was stirred for 15 minutes, and then into the resultant mixture, a mixture of 7.5 g of MMA, 5 g of nBMA, 7.5 g of EHMA, and 30 g of DAMA was added dropwise, and the reaction was continued for 1 hour. After that, GC was measured, and after the confirmation of the disappearance of monomers, 3.6 g of epichlorohydrin was added into the resultant mixture, and the mixture was stirred for 2 hours. After that, the reaction temperature was raised up to 25° C. over 2 hours, and then 100 mL of water was placed in the flask to wash it with water, layer separation was performed and the water layer was removed, subsequently the resultant solution was adjusted to a PGMEA solution having a concentration of 40% by mass by solvent substitution via vacuum concentration. In this way, a random copolymer a-1 having an epoxy group at the terminal and having repeating units derived from DAMA, MMA, nBMA, and EHMA was obtained. The Mw (weight average molecular weight) of the obtained polymer was 2020, and the Mw/Mn (molecular weight distribution) was 1.21.

Next, into 100.0 g of the obtained 40% by mass polymer solution, 7.0 g of polyethyleneimine 300 (PEI 300), 0.2 g of triphenylphosphine, and 30.0 g of propylene glycol monomethyl ether were added, and the resultant mixture was reacted at 45° C. for 25 hours to react the polymer a-1 with the polyethyleneimine Next, to the resultant mixture, 11.5 g of benzyl chloride was added, and then the mixture was gently stirred, the temperature of the polymer solution was raised to 75° C., this temperature was maintained for 8 hours, and the dimethylamino group derived from DAMA was partially converted to quaternary ammonium. The reaction mixture was measured by HPLC, and it was confirmed that the peak derived from benzyl chloride was disappeared. In this way, a polymer in which repeating units derived from DAMA, MMA, nBMA, and EHMA were provided in the side chain of polyethylene imine, and a part thereof was converted to quaternary ammonium was obtained. The obtained polymer was regarded as a "polymer (A-1)".

Synthesis Example 2

Into a 300 mL flask, 125 mL of THF, 1.31 g of lithium chloride, and 23.5 mL, of a hexane solution of n-butyllithium (at a concentration of 1.6 mol/L) were added, the resultant mixture was cooled down to −60° C., and then into the cooled mixture, 3.8 g of diisopropylamine was added, and the mixture was stirred for 15 minutes. Subsequently, into the resultant mixture, 3.8 g of methyl isobutyrate was added and the mixture was stirred for 15 minutes, and then into the resultant mixture, a mixture of 5.5 g of MMA, 4 g of nBMA, 5.5 g of EHMA, and 35 g of DAMA was added dropwise, and the reaction was continued for 30 minutes. After that, GC was measured, and after the confirmation of the disappearance of monomers, 3.6 g of epichlorohydrin was added into the resultant mixture, and the mixture was stirred for 2 hours, and then the temperature was raised up to 25° C. over 2 hours. Subsequently, it was washed with 100 mL of water to perform layer separation, and the water layer was removed, and then the resultant solution was adjusted to a PGMEA solution having a concentration of 40% by mass by solvent substitution via vacuum concentration. In this way, a random copolymer a-2 having an epoxy group at the terminal and having repeating units derived from DAMA, MMA, nBMA, and EHMA was obtained. The Mw (weight average molecular weight) of the obtained polymer was 1980, and the Mw/Mn (molecular weight distribution) was 1.23.

Next, into 100.0 g of the obtained 40% by mass polymer solution, 13.9 g of polyethyleneimine 600 (PEI 600), 0.2 g of triphenylphosphine, and 40.0 g of propylene glycol monomethyl ether were added, and the resultant mixture was reacted at 60° C. for 20 hours to react the polymer a-2 with the polyethyleneimine. Next, to the resultant mixture, 16.3 g of benzyl chloride, and 40.0 g of propylene glycol monomethyl ether were added, and then the mixture was gently stirred, the temperature of the polymer solution was raised to 75° C., this temperature was maintained for 8 hours, and the dimethylamino group derived from DAMA was partially converted to quaternary ammonium. The reaction mixture was measured by HPLC, and it was confirmed that the peak derived from benzyl chloride was disappeared. In this way, a polymer in which repeating units derived from DAMA, MMA, nBMA, and EHMA were provided in the side chain of polyethyleneimine, and a part thereof was converted to quaternary ammonium was obtained. The obtained polymer was regarded as a "polymer (A-2)".

Synthesis Example 3

Into a 300 mL flask, 125 mL of THF, 1.31 g of lithium chloride, and 3.8 g of diisopropylamine were added, and the resultant mixture was cooled down to −60° C. Subsequently, into the cooled mixture, 18.8 mL of a hexane solution of n-butyllithium (at a concentration of 1.6 mol/L) was added, and the mixture was stirred for 5 minutes, and then into the resultant mixture, 3.4 g of methyl isobutyrate was added, and the mixture was stirred for 15 minutes. Into the resultant mixture, a mixture of 7.5 g of MMA, 5 g of nBMA, 7.5 g of EHMA, and 30 g of DAMA was added dropwise, and the reaction was continued for 15 minutes. After that, GC was measured, and after the confirmation of the disappearance of monomers, 3.5 g of epichlorohydrin was added into the resultant mixture, and the mixture was stirred for 2 hours, and then the temperature was raised up to 25° C. over 2 hours to terminate the reaction. Subsequently, it was washed with 100 mL of water to perform layer separation, and the water layer was removed, and then the resultant solution was adjusted to a PGMEA solution having a concentration of 40% by mass by solvent substitution via vacuum concentration. In this way, a random copolymer a-3 having an epoxy group at the terminal and having repeating units derived from DAMA, MMA, nBMA, and EHMA was obtained. The Mw (weight average molecular weight) of the obtained polymer was 2480, and the Mw/Mn (molecular weight distribution) was 1.25.

Next, into 100.0 g of the obtained 40% by mass polymer solution, 4.7 g of polyethyleneimine 300 (PEI 300), 0.2 g of triphenylphosphine, and 40.0 g of propylene glycol monomethyl ether were added, and the resultant mixture was reacted at 70° C. for 16 hours to react the polymer a-3 with the polyethyleneimine Next, to the resultant mixture, 11.5 g of benzyl chloride was added, and then the mixture was gently stirred, the temperature of the polymer solution was raised to 75° C., this temperature was maintained for 8 hours, and the dimethylamino group derived from DAMA was partially converted to quaternary ammonium. The reaction mixture was measured by HPLC, and it was confirmed that the peak derived from benzyl chloride was disappeared. In this way, a polymer in which repeating units derived from DAMA, MMA, nBMA, and EHMA were provided in the side chain of polyethyleneimine, and a part thereof was converted to quaternary ammonium was obtained. The obtained polymer was regarded as a "polymer (A-3)".

Synthesis Example 4

Into a 300 mL flask, 125 mL of THF, 1.31 g of lithium chloride, and 3.8 g of diisopropylamine were added, the resultant mixture was cooled down to −60° C., and then into the cooled mixture, 23.5 mL of a hexane solution of n-butyllithium (at a concentration of 1.6 mol/L) was added, and the mixture was stirred for 15 minutes. Subsequently, into the resultant mixture, 3.8 g of methyl isobutyrate was added and the mixture was stirred for 15 minutes, and then into the resultant mixture, a mixture of 7.5 g of MMA, 5 g of nBMA, 7.5 g of EHMA, and 30 g of DAMA was added dropwise, and the reaction was continued for 1 hour. After that, GC was measured, and after the confirmation of the disappearance of monomers, 3.6 g of epichlorohydrin was added into the resultant mixture, and the mixture was stirred for 2 hours. After that, the reaction temperature was raised up to 25° C. over 2 hours, and then 100 mL of water was placed in the flask to wash it with water, layer separation was performed and the water layer was removed, subsequently the resultant solution was adjusted to a PGMEA solution having a concentration of 40% by mass by solvent substitution via vacuum concentration. In this way, a random copolymer a-4 having an epoxy group at the terminal and having repeating units derived from DAMA, MMA, nBMA, and EHMA was obtained. The Mw (weight average molecular weight) of the obtained polymer was 2020, and the Mw/Mn (molecular weight distribution) was 1.21.

Next, into 100.0 g of the obtained 40% by mass polymer solution, 5.4 g of phenyl biguanide, 0.2 g of triphenylphosphine, and 30.0 g of propylene glycol monomethyl ether were added, and the resultant mixture was reacted at 70° C. for 16 hours to react the polymer a-4 with the phenyl biguanide. Next, to the resultant mixture, 11.5 g of benzyl chloride was added, and then the mixture was gently stirred, the temperature of the polymer solution was raised to 75° C., this temperature was maintained for 8 hours, and the dimethylamino group derived from DAMA was partially converted to quaternary ammonium. The reaction mixture was measured by HPLC, and it was confirmed that the peak derived from benzyl chloride was disappeared. In this way, a polymer in which a partial structure derived from phenyl biguanide, and repeating units derived from DAMA, MMA, nBMA, and EHMA were provided, and a part thereof was converted to quaternary ammonium was obtained. The obtained polymer was regarded as a "polymer (A-4)".

Synthesis Example 5

Into a 300 mL flask, 125 mL of THF, 1.31 g of lithium chloride, and 3.8 g of diisopropylamine were added, the resultant mixture was cooled down to −60° C., and then into the cooled mixture, 23.5 mL of a hexane solution of n-butyl-lithium (at a concentration of 1.6 mol/L) was added, and the mixture was stirred for 15 minutes. Subsequently, into the resultant mixture, 3.8 g of methyl isobutyrate was added and the mixture was stirred for 15 minutes, and then into the resultant mixture, a mixture of 7.5 g of MMA, 5 g of nBMA, 7.5 g of EHMA, and 30 g of DAMA was added dropwise, and the reaction was continued for 1 hour. After that, GC was measured, and after the confirmation of the disappearance of monomers, 3.6 g of epichlorohydrin was added into the resultant mixture, and the mixture was stirred for 2 hours. After that, the reaction temperature was raised up to 25° C. over 2 hours, and then 100 mL of water was placed in the flask to wash it with water, layer separation was performed and the water layer was removed, subsequently the resultant solution was adjusted to a PGMEA solution having a concentration of 40% by mass by solvent substitution via vacuum concentration. In this way, a random copolymer a-5 having an epoxy group at the terminal and having repeating units derived from DAMA, MMA, nEMA, and EHMA was obtained. The Mw (weight average molecular weight) of the obtained polymer was 2020, and the Mw/Mn (molecular weight distribution) was 1.21.

Next, into 100.0 g of the obtained 40% by mass polymer solution, 5.8 g of 1-(o-tolyl)biguanide, 0.2 g of triphenylphosphine, and 30.0 g of propylene glycol monomethyl ether were added, and the resultant mixture was reacted at 70° C. for 16 hours to react the polymer a-5 with the 1-(o-tolyl)biguanide. Next, to the resultant mixture, 11.5 g of benzyl chloride was added, and then the mixture was gently stirred, the temperature of the polymer solution was raised to 75° C., this temperature was maintained for 8 hours, and the dimethylamino group derived from DAMA was partially converted to quaternary ammonium. The reaction mixture was measured by HPLC, and it was confirmed that the peak derived from benzyl chloride was disappeared. In this way, a polymer in which a partial structure derived from 1-(o-tolyl)biguanide, and repeating units derived from DAMA, MMA, nBMA, and EHMA were provided, and a part thereof was converted to quaternary ammonium was obtained. The obtained polymer was regarded as a "polymer (A-5)".

Synthesis Example 6

Into a 300 mL flask, 125 mL of THF, 1.31 g of lithium chloride, and 3.8 g of diisopropylamine were added, the resultant mixture was cooled down to −60° C., and then into the cooled mixture, 23.5 mL of a hexane solution of n-butyl-lithium (at a concentration of 1.6 mol/L) was added, and the mixture was stirred for 15 minutes. Subsequently, into the resultant mixture, 3.8 g of methyl isobutyrate was added and the mixture was stirred for 15 minutes, and then into the resultant mixture, a mixture of 7.5 g of MMA, 5 g of nBMA, 7.5 g of EHMA, and 30 g of DAMA was added dropwise, and the reaction was continued for 1 hour. After that, GC was measured, and after the confirmation of the disappearance of monomers, 3.6 g of epichlorohydrin was added into the resultant mixture, and the mixture was stirred for 2 hours. After that, the reaction temperature was raised up to 25° C. over 2 hours, and then 100 mL of water was placed in the flask to wash it with water, layer separation was performed and the water layer was removed, subsequently the resultant solution was adjusted to a PGMEA solution having a concentration of 40% by mass by solvent substitution via vacuum concentration. In this way, a random copolymer a-6 having an epoxy group at the terminal and having repeating units derived from DAMA, MMA, nBMA, and EHMA was obtained. The Mw (weight average molecular weight) of the obtained polymer was 2020, and the Mw/Mn (molecular weight distribution) was 1.21.

Next, into 100.0 g of the obtained 40% by mass polymer solution, 6.6 g of bis(4-aminophenylethyl) adipate, 0.2 g of triphenylphosphine, and 30.0 g of propylene glycol monomethyl ether were added, and the resultant mixture was reacted at 70° C. for 16 hours to react the polymer a-6 with the bis(4-aminophenylethyl) adipate. Next, to the resultant mixture, 11.5 g of benzyl chloride was added, and then the mixture was gently stirred, the temperature of the polymer solution was raised to 75° C., this temperature was maintained for 8 hours, and the dimethylamino group derived from DAMA was partially converted to quaternary ammonium. The reaction mixture was measured by HPLC, and it was confirmed that the peak derived from benzyl chloride was disappeared. In this way, a polymer in which a partial structure derived from bis(4-aminophenylethyl) adipate, and repeating units derived from DAMA, MMA, nBMA, and EHMA were provided, and a part thereof was converted to quaternary ammonium was obtained. The obtained polymer was regarded as a "polymer (A-6)".

Synthesis Example 7

A polymer a-1 was obtained in a similar manner as in Synthesis Example 1. Next, into 100.0 g of the obtained 40% by mass polymer solution, 4.3 g of N-acetyl-L-glutamine, 0.2 g of triphenylphosphine, and 30.0 g of propylene glycol monomethyl ether were added, and the resultant mixture was reacted at 45° C. for 25 hours to react the polymer a-1 with the N-acetyl-L-glutamine. Next, to the resultant mixture, 11.5 g of benzyl chloride was added, and then the mixture was gently stirred, the temperature of the polymer solution was raised to 75° C., this temperature was maintained for 8 hours, and the dimethylamino group derived from DANA was partially converted to quaternary ammonium. The reaction mixture was measured by HPLC, and it was confirmed that the peak derived from benzyl chloride was disappeared. In this way, a polymer in which a partial structure derived from N-acetyl-L-glutamine, and repeating units derived from DANA, MMA, nBMA, and EHMA were provided, and a part thereof was converted to quaternary ammonium was obtained. The obtained polymer was regarded as a "polymer (A-7)".

The copolymerization rate (% by mass) to each of the monomers in the polymers a-1 to a-6 obtained in the above respective synthesis examples, and the content ratio (parts by mass) of epichlorohydrin to 100 parts by mass of the total amount of monomers are shown in Table 1.

Further, the Mw and the Mw/Mn of each of the polymers a-1 to a-6 are shown in Table 1.

TABLE 1

|  | Polymer a-1 | Polymer a-2 | Polymer a-3 | Polymer a-4 | Polymer a-5 | Polymer a-6 |
|---|---|---|---|---|---|---|
| DAMA (% by mass) | 60.0 | 70.0 | 60.0 | 60.0 | 60.0 | 60.0 |
| MMA (% by mass) | 15.0 | 11.0 | 15.0 | 15.0 | 15.0 | 15.0 |
| nBMA (% by mass) | 10.0 | 8.0 | 10.0 | 10.0 | 10.0 | 10.0 |
| EHMA (% by mass) | 15.0 | 11.0 | 15.0 | 15.0 | 15.0 | 15.0 |
| Repeating units in total (% by mass) | 100 | 100 | 100 | 100 | 100 | 100 |
| Epichloro-hydrin (parts by mass) | 7.2 | 7.2 | 7.0 | 7.2 | 7.2 | 7.2 |
| Mw | 2020 | 1980 | 2480 | 2020 | 2020 | 2020 |
| Mw/Mn | 1.21 | 1.23 | 1.25 | 1.21 | 1.21 | 1.21 |

Comparative Synthesis Example 1

Into a 300 mL flask, 125 mL of THF, and 2.62 g of lithium chloride were added, and the resultant mixture was cooled down to 60° C. Into the cooled mixture, 23.5 mL of a hexane solution of n-butyllithium (at a concentration of 1.6 mol/L) was added, and the mixture was stirred for 5 minutes, and then into the resultant mixture, diphenylethylene (6.8 g) was added, and the mixture was stirred for 15 minutes. Into the resultant mixture, a mixture of 7.5 g of MMA, and 5 g of nBMA was added dropwise, and the reaction was continued for 15 minutes. GC was measured, and after the confirmation of the disappearance of monomers, 7.5 g of EHMA was added dropwise into the resultant mixture, and the reaction was continued for 15 minutes after the dropwise addition. GC was measured, and the disappearance of monomers was confirmed. Next, 30 g of DAMA was added dropwise into the resultant mixture, and the reaction was continued for 30 minutes after the dropwise addition. GC was measured, and after the confirmation of the disappearance of monomers, 2 g of ethanol was added into the resultant mixture to terminate the reaction. After that, the resultant solution was adjusted to a PGMEA solution having a concentration of 40% by mass by vacuum concentration. In this way, a block copolymer including a block A having a repeating unit derived from DAMA, a block B1 having a repeating unit derived from EHMA, and a block B2 having repeating units derived from MMA and nEMA was obtained. The Mw (weight average molecular weight) of the obtained polymer was 1100, and the Mw/Mn (molecular weight distribution) was 1.2.

Next, into 100 g of the obtained polymer solution, 13.1 g of benzyl chloride, and 30.0 g of propylene glycol monomethyl ether were added, and then the mixture was gently stirred, the temperature of the polymer solution was raised to 90° C., this temperature was maintained for 8 hours, and the dimethylamino group derived from DAMA was partially converted to quaternary ammonium. The reaction mixture was measured by HPLC, and it was confirmed that the peak derived from benzyl chloride was disappeared. In this way, a block copolymer including a block A having a repeating unit derived from DAMA, of which a part was converted to quaternary ammonium; a block B1 having a repeating unit derived from EHMA; and a block B2 having repeating units derived from MMA and nBMA was obtained. The obtained copolymer was regarded as a "polymer (P-1)".

The polymers (polymer a-1 to polymer a-6, and polymer p-1) providing respective polymer chains, the compounds providing respective specific partial structures, and the use ratio of benzyl chloride, which were used in each of the above Synthesis Examples and Comparative Synthesis Example, are shown in Table 2.

TABLE 2

|  | Synthesis Example 1 (A-1) | Synthesis Example 2 (A-2) | Synthesis Example 3 (A-3) | Synthesis Example 4 (A-4) | Synthesis Example 5 (A-5) | Synthesis Example 6 (A-6) | Synthesis Example 7 (A-7) | Comparative Synthesis Example 1 (P-1) |
|---|---|---|---|---|---|---|---|---|
| Polymers a-1 to a-6, or polymer p-1 (parts by mass) | 40 | 40 | 40 | 40 | 40 | 40 | 40 | 40 |
| PEI 300 (parts by mass) | 7.0 | — | 4.7 | — | — | — | — | — |
| PEI 600 (parts by mass) | — | 13.9 | — | — | — | — | — | — |
| Phenyl biguanide (parts by mass) | — | — | — | 5.4 | — | — | — | — |
| 1-(o-Tolyl)biguanide (parts by mass) | — | — | — | — | 5.8 | — | — | — |
| Bis(4-aminophenylethyl) adipate (parts by mass) | — | — | — | — | — | 6.6 | — | — |
| N-acetyl-L-glutamine (parts by mass) | — | — | — | — | — | — | 4.3 | — |
| Benzyl chloride (parts by mass) | 11.5 | 16.3 | 11.5 | 11.5 | 11.5 | 11.5 | 11.5 | 13.1 |
| Ratio with respect to DAMA (eq) | 0.8 | 0.9 | 0.8 | 0.8 | 0.8 | 0.8 | 0.8 | 0.8 |

Test Example 1

Antimicrobial and Disinfecting Properties Test

Into 500 mL of hexane, 10 g of the polymer obtained in each of the above Synthesis Examples was added dropwise over 2 hours, and then vacuum drying was performed at 40° C. for 24 hours. The powder thus obtained was used for a test.

Example 1

(Preparation of Liquid Medium)
30.4 g of a medium (Mueller Hinton II) was weighed out, and dissolved in 800 mL of sterile water, and the resultant mixture was subjected to an autoclave treatment at 121° C. and 2 atm for 15 minutes.
(Preparation of Bacterial Liquid)
Each of the bacteria of the following (1) to (8) was suspended in 1 mL of the liquid medium obtained in the above "preparation of liquid medium", OD600 was measured, and a liquid medium was added so that the amount of bacteria is $1\times10^8$ cfu/mL to prepare each of the bacterial liquids.
(1) *E. coli* (drug sensitive strain, DH5α)
(2) *S. aureus* (drug sensitive strain, ATCC29213)
(3) *E. coli* (NDM-1 producing strain)
(4) *E. coli* (IMP-1 producing strain, ST131)
(5) *Klebsiella pneumoniae* (KPC-2 producing strain, ST258)
(6) *A. baumannii* (OXA-23 producing strain, ST2)
(7) *Pseudomonas aeruginosa* (MP-1 producing strain, ST235)
(8) MRSA (*S. aureus* methicillin-resistant strain)
(Measurement)
A polymer (A-1) and water were mixed to prepare 10 mg/mL of a polymer aqueous solution. Into 897.6 μL of the prepared liquid medium, 102.4 μL of the above-described polymer aqueous solution was added so that the concentration of the polymer is 1024 μg/mL. This solution was diluted 2 times in wells of a 96-well plate to prepare a dilution series of 1024 μg/mL to 0.015625 μg/mL. Next, 5 μL of a bacterial liquid was added to each of the wells and incubated at 37° C. for 16 hours.

The turbidity of each of the wells was visually discriminated and the growing state of the bacteria was confirmed. The concentrations of the dilution series, at which it was visually determined that the antimicrobial action and disinfecting action were performed without cloudiness, are shown in Table 3.

Examples 2 to 7 and Comparative Examples 1 to 4

The antimicrobial and the disinfecting properties were evaluated in a similar manner as in Example 1 except that each of the compounds shown in Table 3 was used in place of the polymer (A-1) in Example 1. The evaluation results are shown in Table 3. In this regard, in the Table, PEI 300 means polyethyleneimine 300 and PEI 600 means polyethyleneimine 600, respectively.

TABLE 3

|  |  | Compound | *E. coli* (Drug sensitive strain, DH5α) | *S. aureus* (Drug sensitive strain, ATCC29213) | *E. coli* (NDM-1 producing strain) | *E. coli* (IMP-1 producing strain, ST131) | *Klebsiella pneumoniae* (KPC-2 producing strain, ST258) | *A. baumannii* (OKA-23 producing strain, ST2) | *Pseudomonas aeruginosa* (MP-1 producing strain, ST235) | MRSA |
|---|---|---|---|---|---|---|---|---|---|---|
| Examples | 1 | Polymer (A-1) | 64 | 64 | 16 | 64 | 128 | 64 | 128 | 64 |
|  | 2 | Polymer (A-2) | 64 | 64 | 128 | 128 | 128 | 128 | 64 | 64 |
|  | 3 | Polymer (A-3) | 32 | 64 | 32 | 32 | 64 | 64 | 64 | 16 |
|  | 4 | Polymer (A-4) | 32 | 64 | 16 | 64 | 256 | 32 | 1024 | 16 |
|  | 5 | Polymer (A-5) | 32 | 64 | 16 | 64 | 256 | 64 | 1024 | 16 |
|  | 6 | Polymer (A-6) | 16 | 64 | 16 | 32 | 64 | 32 | 256 | 16 |
|  | 7 | Polymer (A-7) | 64 | 128 | 8 | 128 | 16 | 64 | 1024 | 32 |
| Comparative | 1 | PEI300 | 256 | 512 | 512 | 512 | 512 | >1024 | 32 | >1024 |
| Examples | 2 | PEI600 | 256 | 512 | 512 | 512 | 512 | >1024 | >1024 | >1024 |
|  | 3 | Phenyl biguanide | >1024 | >1024 | 1024 | 1024 | >1024 | 1024 | >1024 | >1024 |
|  | 4 | Polymer (P-1) | 32 | 128 | 32 | — | >1024 | 256 | >1024 | 256 |

As shown in Table 3, the polymers (A-1) to (A-7) had antimicrobial and disinfecting properties against a wide range of kinds of germs. Of these, the polymers (A-1) to (A-3), and (A-6), particularly the polymers (A-1) to (A-3) had excellent antimicrobial and disinfecting properties even against *Pseudomonas aeruginosa*.

Test Example 2

Cytotoxicity Test

The cytotoxicity of the polymer (A-3) was evaluated using a CCK-8 assay kit (DOJINDO LABORATORIES). That is, HepG2 cells were inoculated at 10,000 cells/well in a 96-well cell culture plate (manufactured by IWAKI), and cultured for 24 hours in Dulbecco's MEM containing 10% by mass serum. The polymer (A-3) was made into an aqueous solution of 10 mg/mL, and the final concentration was adjusted to 3 kinds of 1000, 100, and 10 μg/mL with Dulbecco's MEM containing 10% by mass serum. The medium of the cultured plate was removed with an aspirator, and the medium solution containing the polymer (A-3) was added to each of the wells so as to be n=3, and cultured for 24 hours. A CCK-8 reagent was added to each of the wells at 10 μL/well, and after 2 hours cultivation, the absorbance in 450 nm (ref 598 nm) was measured to determine the cell viability for the positive control without the addition of the polymer. The results of the cytotoxicity test are shown in the following Table 4.

TABLE 4

| Polymer concentration (μg/mL) | Cell viability (%) |
|---|---|
| 1000 | 14.1 |
| 100 | 9.1 |
| 10 | 106.7 |

The invention claimed is:

1. A polymer, comprising:
a polymer chain ending with a terminal compound and bonded to the terminal compound with a —NH— group present in the compound;
wherein the compound comprises a plurality of —NH— groups,
wherein the polymer chain comprises a repeating unit of formula (1) and a repeating unit of formula (2):

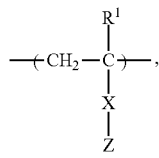
(1)

wherein
$R^1$ represents a hydrogen atom or a methyl group,
Z represents an organic ammonium salt or an organic ammonium salt and —$NR^5R^6$,
wherein $R^5$ and $R^6$ each independently represent a hydrogen atom, or a substituted or unsubstituted hydrocarbon group,
the organic ammonium salt is selected from the group consisting of —$N^+R^2R^3R^4Y^{y-}$, —(C=O)$O^-N^+HR^2R^3R^4$, and —(C=O)$O^{--}A^+$ wherein $R^2$ to $R^4$ each independently represent a hydrogen atom, a substituted or unsubstituted hydrocarbon group, $Y^{y-}$ represents a y-valent counter anion, and $A^+$ represents a quaternary ammonium cation,
and
X represents a single bond, a methylene group, an alkylene group, —(C=O)$OR^{11}$-(*), or —(C=O)$NHR^{12}$-(*) wherein $R^{11}$ and $R^{12}$ each represent a methylene group, an alkylene group, or an alkylene oxyalkylene group, and "*" represents a chemical bond bonded to the Z;

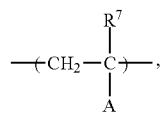
(2)

wherein
$R^7$ represents a hydrogen atom or a methyl group, and
A represents an aromatic hydrocarbon group, —(C=O)$OR^8$, —(C=O)$NHR^9$, or —$OR^{10}$, wherein $R^8$ to $R^{10}$ each represent a hydrocarbon group or a group having a chain ether structure or a cyclic ether structure.

2. The polymer according to claim 1, wherein a weight average molecular weight (Mw) of the polymer chain is 3,000 or less in terms of polystyrene measured by gel permeation chromatography, wherein a mobile phase is tetrahydrofuran.

3. The polymer according to claim 1, wherein
Z is an organic ammonium salt of formula —$N^+R^2R^3R^4Y^{y-}$, wherein $R^2$ to $R^4$ each independently represent a hydrogen atom, or a substituted or unsubstituted hydrocarbon group, and $Y^{y-}$ represents a y-valet counter anion, or
Z is an organic ammonium salt of formula —$N^+R^2R^3R^4Y^{y-}$ and —$NR^5R^6$.

4. The polymer according to claim 1, wherein X is —(C=O)$OR^{11}$-(*), —(C=O)$NHR^{12}$-(*), and
wherein $R^{11}$ and $R^{12}$ each represent a methylene group, an alkylene group, or an alkylene oxyalkylene group.

5. The polymer according to claim 1, wherein the compound is a compound comprising at least one selected from the group consisting of a primary amino group, a secondary amino group, and a carbamoyl group.

6. The polymer according to claim 1, wherein the compound is a polyaziridine-polymer, a modified polyaziridine polymer, a diamine compound, a biguanide compound, an amino acid, an N-acylamino acid, a peptide, an amino sugar, a polyamine sugar, or an antimicrobial drug.

7. The polymer according to claim 1, wherein the terminal compound further comprises a divalent group formed by ring opening of a cyclic ether group bonded to a —NH— group which is different from the group bonded to the polymer chain end.

8. An antimicrobial agent, a disinfectant, or an antimicrobial and disinfecting agent, comprising the polymer according to claim 1 as an active component.

9. An antimicrobial material, a disinfectant material, or an antimicrobial and disinfecting material, comprising the polymer according to claim 1.

10. An antimicrobial method, a disinfecting method, or an antimicrobial and disinfecting method, comprising providing an antimicrobial and/or disinfecting property with the polymer according to claim 1.

11. The polymer according to claim 1, wherein a content of the repeating unit (1) wherein Z is an organic ammonium salt is 60% by mole or more.

* * * * *